(12) United States Patent
Fram

(10) Patent No.: US 10,395,762 B1
(45) Date of Patent: Aug. 27, 2019

(54) CUSTOMIZED PRESENTATION OF DATA

(75) Inventor: Evan K. Fram, Paradise Valley, AZ (US)

(73) Assignee: MERGE HEALTHCARE SOLUTIONS INC., Hartland, WI (US)

(*) Notice: Subject to any disclaimer, the term of this patent is extended or adjusted under 35 U.S.C. 154(b) by 606 days.

(21) Appl. No.: 13/495,991

(22) Filed: Jun. 13, 2012

Related U.S. Application Data

(60) Provisional application No. 61/496,973, filed on Jun. 14, 2011.

(51) Int. Cl.
*G16H 10/00* (2018.01)
*G16H 15/00* (2018.01)

(52) U.S. Cl.
CPC ............. *G16H 10/00* (2018.01); *G16H 15/00* (2018.01)

(58) Field of Classification Search
CPC ....... G06Q 50/22–50/24; G06F 19/321; G16H 10/00; G16H 15/00
USPC .......................................................... 705/2–3
See application file for complete search history.

(56) References Cited

U.S. PATENT DOCUMENTS

| | | | | |
|---|---|---|---|---|
| 5,452,416 | A * | 9/1995 | Hilton et al. | 715/783 |
| 5,767,854 | A | 6/1998 | Anwar | |
| 7,685,262 | B2 * | 3/2010 | Choubey et al. | 709/220 |
| 8,019,626 | B2 * | 9/2011 | Mahesh et al. | 705/3 |
| 8,078,749 | B2 | 12/2011 | Khosravy | |
| 8,543,415 | B2 * | 9/2013 | Venon et al. | 705/2 |
| 8,867,807 | B1 | 10/2014 | Fram | |
| 2003/0005140 | A1 | 1/2003 | Dekel et al. | |
| 2004/0077952 | A1 * | 4/2004 | Rafter et al. | 600/481 |
| 2004/0095349 | A1 | 5/2004 | Bito et al. | |
| 2004/0136404 | A1 | 7/2004 | Mahonen et al. | |
| 2004/0146221 | A1 * | 7/2004 | Siegel et al. | 382/305 |
| 2005/0108060 | A1 * | 5/2005 | Sasano | 705/3 |
| 2006/0007244 | A1 | 1/2006 | Matsumoto | |
| 2006/0093207 | A1 | 5/2006 | Reicher et al. | |
| 2006/0170954 | A1 | 8/2006 | Leyvi | |
| 2006/0190572 | A1 | 8/2006 | Novik et al. | |
| 2006/0215569 | A1 | 9/2006 | Khosravy et al. | |
| 2006/0230067 | A1 | 10/2006 | Tarnoff et al. | |
| 2007/0053567 | A1 * | 3/2007 | Adachi et al. | 382/128 |
| 2007/0106683 | A1 | 5/2007 | Grabelsky et al. | |
| 2008/0069397 | A1 * | 3/2008 | Bartsch | 382/100 |
| 2009/0089448 | A1 | 4/2009 | Sze et al. | |
| 2009/0182577 | A1 * | 7/2009 | Squilla et al. | 705/2 |
| 2010/0131294 | A1 * | 5/2010 | Venon et al. | 705/3 |
| 2011/0231209 | A1 * | 9/2011 | Maresh et al. | 705/3 |
| 2012/0095953 | A1 * | 4/2012 | Schmidt et al. | 706/52 |
| 2012/0124517 | A1 | 5/2012 | Landry et al. | |

OTHER PUBLICATIONS

U.S. Appl. No. 14/488,166, filed Sep. 16, 2014, Fram.

(Continued)

*Primary Examiner* — Sheetal R Paulson
(74) *Attorney, Agent, or Firm* — Michael Best & Friedrich LLP

(57) ABSTRACT

Provided herein are various systems and methods for monitoring how users interact with medical imaging exams to automatically determine the view order and importance of various series within medical imaging exams as a function of a particular user, exam type, clinical information, and/or other characteristic of medical data.

21 Claims, 15 Drawing Sheets

(56) References Cited

OTHER PUBLICATIONS

AGFA HealthCare, color brochure "IMPAX 6: Digital Image and Information Management," ©2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. ©2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from http://resources.dominator.com/assets/004/6999.pdf. Document accessed Feb. 9, 2015.
DR Systems, DR Scheduler User Guide, Release 8.2, 410 pages, (TCP-000115-A), © 19972009, DR Systems, Inc. Downloaded from http://resources.dominator.com/assets/003/6850.pdf. Document accessed Feb. 9, 2015.
Fujifilm Medical Systems, Synapse® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, Synapse® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, Synapse® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http:www3.gehealthcare.com/en/products/categoriesthealthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://wvvw.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 pages, color brochure, (BRO80809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at httb://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imaging and PACS | McKesson, 1 page (color) printout. Accessed at http://www.mckesson.com/providers/health-systems/diagnostic-imagine/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/risbacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.

(56) References Cited

OTHER PUBLICATIONS

PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging.informatics/isite_pacs. Accessed on Feb. 9, 2015.
RamSoft, RIS PACS Teleradiology, PowerServer Pacs, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigital/Imaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.

* cited by examiner

| | Acute Stroke | Multiple Sclerosis | Tumor Follow-up |
|---|---|---|---|
| Sagittal T1 | | | |
| Axial T1 | | | |
| Axial FLAIR | 80% | 95% | 80% |
| Axial T2 | | | |
| Axial Diffusion | 95% | | |
| Coronal GRE | 55% | | |
| Sagittal FLAIR | | 75% | |
| Axial T1 +C | | 25% | 95% |
| Coronal T1 +C | | | 75% |
| Sagittal T1 +C | | | 30% |

US 10,395,762 B1

CUSTOMIZED PRESENTATION OF DATA

CROSS-REFERENCE TO RELATED APPLICATIONS

This application claims the benefit of priority under 35 U.S.C. § 119(e) of U.S. Provisional Application No. 61/496,973, filed Jun. 14, 2011, the disclosure of which is hereby incorporated by reference in its entirety.

BACKGROUND

There is a need for innovations that increase the efficiency and accuracy of interpretation of medical imaging exams.

SUMMARY

Provided herein are various systems and methods for monitoring how users interact with medical imaging exams to automatically determine the view order and importance of various series within medical imaging exams as a function of a particular user, exam type, clinical information, and/or other characteristic of medical data.

In one embodiment, a method of ordering a plurality of image series of a medical exam comprises determining an exam characteristic associated with a medical exam, accessing interaction data of a user of a computing device, the computing device comprising one or more computer processors, the interaction data storing associations between exam characteristics and respective orders in which series of images associated with respective exam characteristics were selected for display by the user, and determining, based on interaction data indicating respective orders in which series of images associated with the determined exam characteristic were viewed, a custom ordering of the series of the exam.

In some embodiments, the exam characteristic comprises one or more of an exam type, exam modality, clinical indication and/or other clinical information, medical history of a patient, or risk factors associated with the patient. In some embodiments, the computing device is configured to display images of the plurality of series in an order indicated in the custom ordering. In some embodiments, the computing device is configured to preload, process with computer aided diagnostics, and/or generate reconstructions of images of the plurality of series in an order indicated in the custom ordering. In some embodiments, the method further includes accessing interaction data of the user of the computing device, the interaction data storing associations between exam characteristics and relative importance levels of respective series associated with exams having respective exam characteristics, wherein the custom ordering of the series of the exam is further based on the importance levels associated with the determined exam characteristic. In some embodiments, the importance level of respective series is based on one or more of a number of images of respective series that are added to a montage, a number of images of the respective series that are marked as key images, an order in which respective series are selected for display, a frequency that images of respective series are used for measurements, or a frequency that images for respective series are selected for inclusion in a report. In some embodiments, the interaction data further includes interaction data of other users.

In one embodiment, a method comprises determining one or more characteristics of an exam to be used in determining a custom ordering of respective series of images of the exam, identifying interaction data associated with the determined one or more characteristics of the exam, the interaction data indicating interactions of one or more users with images of respective image series of other exams having the determined one or more characteristics, and determining, based on the identified interaction data, a custom ordering of series of the exam.

In some embodiments, the one or more characteristics are determined based on user preferences, group preferences, site preferences, system preferences, and/or default software preferences. In some embodiments, the one or more characteristics comprise one or more of an exam type, exam modality, clinical indication and/or other clinical information, medical history of a patient, or risk factors associated with the patient. In some embodiments, the one or more characteristics comprise only a type of the exam. In some embodiments, the one or more characteristics comprise only clinical indication of the exam. In some embodiments, the one or more users comprise only the user. In some embodiments, the one or more users comprise one or more other users. In some embodiments, the one or more other users comprise users associated with a same group as the user, users associated with a same specialty as the user, and/or users designated as experts with reference to exams having the determined one or more characteristics. In some embodiments, the method further includes determining the interaction data based on an order in which the one or more users selected for display respective image series of other exams having the determined one or more characteristics. In some embodiments, the method further includes determining the interaction data based on data indicating which images series of other exams having the determined one or more characteristics include images that are marked as key images or selected for inclusion in a montage. In some embodiments, the data comprises importance scores for respective series associated with exams having the determined one or more characteristics. In some embodiments, importance scores for respective image series are weighted based on a quantity of images of respective image series that are marked as key images or selected for inclusion in a montage. In some embodiments, the method further includes using the determined custom ordering as an order of displaying series of the exam, preloading series of the exam, processing series of the exam with computer aided diagnostics, and/or generating reconstructions of images of series of the exam. In some embodiments, use of the determined custom ordering is determined based on user preferences, group preferences, site preferences, system preferences, and/or default software preferences.

BRIEF DESCRIPTION OF THE DRAWINGS

FIG. 4a illustrates example arrangements of image series of an exam, in particular, a brain MRI in the example of FIG. 4a.

DETAILED DESCRIPTION

Figure 1:
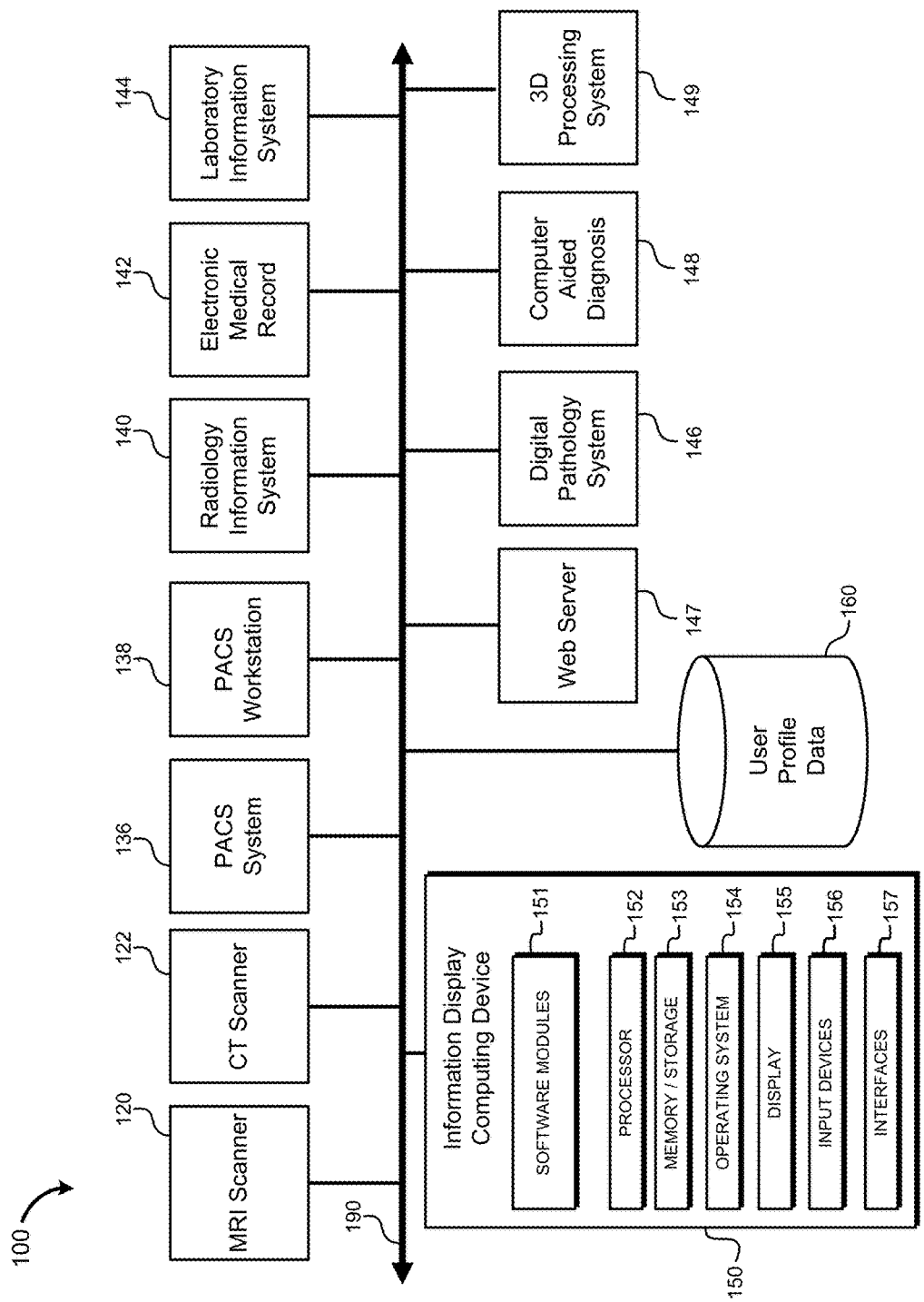
FIG. 1 is a system diagram which shows various components of a system configured for displaying information utilizing certain systems and methods described herein.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device. Users may include, for example, doctors, radiologists, hospital staff, or other individuals involved in acquisition, analysis, storage, management, or other tasks related to medical images. In other embodiments, users may include any individuals or groups of individuals that generate, transmit, view, and/or otherwise work with images of any type. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a tangible computer readable medium, such as a compact disc, digital video disc, flash drive, hard drive, memory device or any other tangible medium. Such software code may be stored, partially or fully, on a memory of a computing device (e.g., RAM, ROM, etc.), such as the computing system 150 (see discussion of FIG. 1, below), and/or other computing devices illustrated in the figures, in order to perform the respective methods. For ease of explanation, the methods will be described herein as performed by the computing system 150, but the methods are not limited to performance by the computing system 150 and should be interpreted to include performance by any one or more of the computing devices noted herein and/or any other suitable computing device.

Definitions

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Medical imaging exam: Medical imaging exams comprise data related to a medical procedure, such as medical images, medical reports, and/or related information. Medical imaging exams can be acquired by a number of different medical imaging techniques, including computed tomography (CT), magnetic resonance imaging (MRI), ultrasound, nuclear medicine, positron emission computed tomography (PET), digital angiography, mammography, computed radiography, digital radiography, fluoroscopy, images generated in medical pathology and endoscopy, and any other imaging techniques. Medical imaging exams may also include text reports, graphs, numerical information such as measurements, movies, sounds or voice data, and/or any other information that may be stored in digital format. Although much of the discussion herein is with reference to medical imaging exams, the systems and methods described may be used with other types of images and data. Thus, any reference to medical images may alternatively be construed to cover any other type of image.

Series: Medical imaging exams are typically organized into one or more series, with each series including one or more images. Images in a series typically share one or more common characteristic, for example the type of anatomic plane and/or image orientation. Series may be characterized by their type. For example, series may be acquired using different pulse sequences, acquired in different anatomic planes, and acquired before or after administration of intravenous contrast material. In some embodiments a series may include other types of information, such as text reports, graphs, numerical information such as measurements, movies, sounds or voice data, and/or any other information that may be stored in digital format.

Hanging Protocol: A hanging protocol indicates, and may be used to determine, a layout of series on one or more computer displays. For example, a user may prefer the arrangement shown in view 1310 of FIG. 13 for display of brain MRI exams, where the Sagittal T1 series is displayed in the top-left frame, the Axial T1 series is displayed in the top-middle frame, etc. The user may prefer different arrangements on the basis of a variety of factors, e.g., exam type, clinical indication, computer hardware, etc.

Interaction Data: Interaction data is information indicating how a user interacts with medical images. For example, interaction data may indicate an order in which a particular viewer views images from various series types. Interaction data may indicate how long a user interacts with particular images, image series, or other pieces of medical data. Interaction data may indicate operations a user performs on particular images, image series, or other pieces of medical data. Interaction data may be user specific (e.g., each user can have a set of interaction data). Interaction data may be associated with a group of users (e.g., a radiology group may have group interaction data, possibly in addition to user specific interaction data, or interaction data may be associated with a subgroup, such as radiologists with expertise in a particular area of radiology). Non-experts may utilize interaction data collected from experts in a field. Thus, a user's interaction data may include interaction data of a particular user and/or interaction data of a group of users. Interaction data may be obtained in various manners, such as by monitoring data that is built into image viewing software (e.g., PACS software) or third-party software that interacts with image viewing software. Interaction data may be stored in any format and made available to software modules that determine adjustments to viewing preferences of a user based on the particular user's (and/or groups to which the user belongs) interaction data.

Series View Order: Series view order is an order in which series of an exam are viewed, such as by a particular user. Irrespective of the way various series are displayed on computing device, as determined by a hanging protocol, for example, a user may view the series in an order that is determined by the particular user's thought process and/or routine, for example. Thus, different users may have different series view orders, even for the same exam type using the same hanging protocol. In addition, a user's routine for viewing the various series may vary depending on the clinical indication for performing the exam, viewing location, viewing device, and/or other information related to the user or patient.

For example, for a brain MRI performed for "Possible Multiple Sclerosis", a user may prefer to first view the Sagittal FLAIR series, followed by the Axial FLAIR series, etc. For a different clinical indication, though, such as "Acute stroke", the same user may routinely view the Axial Diffusion series first as it is the most sensitive series for detection of acute infarction, followed by the Axial FLAIR series, etc. Thus, even if the hanging protocol for the two medical imaging exams is identical, the user may view images of the medical imaging exams in a different order. Thus, series view order may vary among users, change over time for a user, and/or vary for a user based on the clinical information associated with the exam and/or other information regarding the user, the viewing environment, and/or the exam.

In various embodiments described herein, a series view order may be:

Determined automatically by a computing device based on the user's interaction data (and/or interaction data of one or more groups). A series view order may be determined upon request of an exam from a user (e.g., in real-time using current interaction data of the user) and/or may be determined based on concurrent or earlier analysis of the user's interaction data or a groups interaction data. For example, a user's series view order may be re-determined monthly, at the user's request, or in response to one or more predefined user or system actions.

Set explicitly or determined automatically for a user, user group, site, etc.

Automatically correlated with clinical information (or other characteristic of an exam) so that a different series view order may be associated with different clinical information (or other characteristic of an exam).

Used by the computing device to prioritize various operations related to an exam, which may optimize a user's access and/or review of the medical data. For example, if the user accesses a brain MRI with the clinical information "Acute Stroke" and his series view order indicates that the Axial Diffusion series is the first series in his typical series view order for that indication (e.g., based on the user's interaction data), the Axial Diffusion series may be communicated to the user's computing device first. This may increase the speed that the user can access that series, increasing the efficiency of the user. In another embodiment, an exam type may be used to determine the order in which series are transmitted, processed, and/or displayed to the user, regardless of the associated clinical indication (or other clinical information) associated with the exam. Thus, series view order may be associated with various characteristics of exams, such as exam type, exam modality, and/or any clinical information associated with the exam.

Used to determine an order of operations related to image processing that could occur on a client or server, for example, creation of MPR or 3D volumetric rendered images, processing with Computer Aided Diagnosis (CAD) software, etc.

Used to organize the display of information based on a computing device type and/or for a particular computing device. For example, a user may prefer to display only a single image frame when viewing exams on a smartphone, allowing the display of only one series at a time.

Used to determine the order that the various series are displayed, e.g., displaying the series in an order indicated by a series view order.

Series Importance: Series importance is an indication of importance of respective series and/or images within a series. Series importance may be determined based on several factors, discussed below, such as indications of importance of images in respective series that are provided by a particular user and/or other user's that have previously viewed series having similar characteristics (e.g. same series type and clinical indication). In some embodiments, interaction data of a particular user is monitored to determine the relative importance of various series and to determine the series importance for the user.

In medical imaging exams, various series may vary in their sensitivity and specificity for detecting various abnormalities. Once a radiologist has viewed a medical imaging exam, it may be useful to other doctors who may later view the exam (or other similar exams) to be provided a summary of the important findings of the exam in the form of a few selected images. Computing systems used by radiologists to view medical imaging exams may allow users to designate certain images within an exam as "key images." By tracking the frequency that images are chosen by the radiologist from various types of series, the various series may be ranked in terms of "series importance".

In various embodiments, the series importance may be based on the frequency that images within series are viewed, chosen as key images, chosen for inclusion in a montage of selected images that the user chooses to summarize the exam, chosen for inclusion in a report, and/or used for measurements. In other embodiments, additional and/or different interaction data may be used to determine series importance.

Series Importance may vary from user to user and for a single user may vary based on a variety of actions, such as clinical information associated with a patient or a patient's medical exam, for example. In various embodiments described herein, series importance may be:

- Determined automatically by a computing device based on the user's interaction data (and/or interaction data of one or more groups in which the user is a member and/or data of one or more groups in which the user is not a member, e.g. a group of expert users). A series importance may be determined upon request of an exam by a user (e.g., in real-time using current interaction data of the user) and/or may be predetermined based on earlier analysis of the user's interaction data and/or determined based on current analysis of prior interaction data. For example, series importance for respective exam types may be re-determined monthly or at the user's request.
- Set explicitly or determined automatically for a user, user group, site, etc.
- Automatically correlated with clinical information (or other characteristic of an exam) so that a different series importance may be associated with different clinical information (or other characteristic of an exam).
- Used by the computing device to prioritize various operations related to a series or exam (e.g., multiple series), which may optimize a user's access and/or review of the medical data. For example, if the user accesses a brain MRI with the clinical information "Acute Stroke" and the user's series importance indicates that the Axial Diffusion series is the most "important" series for that particular clinical indication, the Axial Diffusion series may be communicated to the computing device first. This may increase the speed that the user can access that series, increasing the efficiency of the user.
- Used to organize the display of information based on a computing device type and/or for a particular computing device. For example, a user may prefer to display only a single image frame when viewing exams on a smartphone, allowing the display of only one series at a time. The series importance may be used to organize the order that the various series are displayed, e.g., displaying the most "important" series first followed by the other series in series view order. This may serve as a form of cognitive augmentation, where the user's attention is directed to the most "important" series first, e.g., a series that has been determined to be of most importance for the particular clinical indication associated with the exam.
- Aggregated among users or groups of users. For example, the series importance data from a group of neuroradiologists may be designated as the "expert series importance" information. This could then be used by less experienced users to guide the presentation of information for that group, a form of cognitive augmentation.

Introduction

As discussed further herein, interaction data of a user may be monitored, stored, and/or used in various manners, such as in order to determine series view order and/or series importance to be used in displaying an exam series to the user. In various embodiments interaction data, as well as data derived from the interaction data, such as series view order and/or series importance, may be used to:

- Automatically organize presentation of exam components (e.g., series of an exam) based on a predicted importance of respective exam components based on interaction data of a user requesting an exam in combination with various other exam, environment, and/or other characteristics, such as exam type, clinical indication, user, user group, or other characteristic of a user or user viewing environment. This may increase efficiency as well as serve as a form of cognitive augmentation by automatically directing the user's attention to the most important components of an exam, e.g., based on clinical information of the exam.
- Enhance reading accuracy and/or evolve exam acquisition protocols.
- Increase system responsiveness and physician efficiency by prioritizing transmission, processing, and/or display of exam series based on the order the user is likely to need the information during viewing of an exam based on the user, exam type, clinical information, etc. This prioritization may be independent of hanging protocols and may be particularly useful for web connections, e.g., mobile, cloud based PACS/EMR, etc.

Example Computing System

FIG. 1 is a system diagram which shows the various components of a system 100 configured for displaying information utilizing certain systems and methods described herein. As shown, the system 100 may include an information display computing device 150 and may include other systems, including those shown in FIG. 1.

The information display computing device 150, also referred to herein as "computing device 150" or "device 150," may take various forms. In one embodiment, the information display computing device 150 may be a computer workstation having information display software modules 151. In other embodiments, software modules 151 may reside on another computing device, such as a web server or other server, and the user directly interacts with a second computing device that is connected to the web server via a computer network. The software modules 151 will be described in detail below.

In one embodiment, the information display computing device 150 comprises a server, a desktop computer, a workstation, a laptop computer, a mobile computer, a smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The information display computing device 150 may run an off-the-shelf operating system 154 such as a Windows, Linux, MacOS, Android, or iOS. The information display computing device 150 may also run a more specialized operating system which may be designed for the specific tasks performed by the computing device 150.

The information display computing device 150 may include one or more computing processors 152. The computer processors 152 may include central processing units (CPUs), and may further include dedicated processors such as graphics processor chips, or other specialized processors. The processors generally are used to execute computer instructions based on the information display software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, Lua, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The information display computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The information display computing device 150 may also include or be interfaced to one or more display devices 155 that provide information to the users. Display devices 155 may include a video display, such as one or more high-resolution computer monitors, or a display device integrated into or attached to a laptop computer, handheld computer, smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The information display computing device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The information display computing device 150 may also include one or more interfaces 157 which allow information exchange between information display computing device 150 and other computers and input/output devices using systems such as Ethernet, Wi-Fi, Bluetooth, as well as other wired and wireless data communications techniques.

The modules of the information display computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of information display computing device 150 may be combined into fewer components and modules or further separated into additional components and modules.

The information display computing device 150 may communicate and/or interface with other systems and/or devices. In one or more embodiments, the computer device 150 may be connected to a computer network 190. The computer network 190 may take various forms. It may be a wired network or a wireless network, or it may be some combination of both. The computer network 190 may be a single computer network, or it may be a combination or collection of different networks and network protocols. For example, the computer network 190 may include one or more local area networks (LAN), wide area networks (WAN), personal area networks (PAN), cellular or data networks, and/or the Internet.

Various devices and subsystems may be connected to the network 190. For example, one or more medical scanners may be connected, such as MRI scanners 120. The MRI scanner 120 may be used to acquire MRI images from patients, and may share the acquired images with other devices on the network 190. The network 190 may also include one or more CT scanners 122. The CT scanners 122 may also be used to acquire images and, like the MRI scanner 120, may then store those images and/or share those images with other devices via the network 190. Any other scanner or device capable of inputting or generating information that can be presented to the user as images, graphics, text or sound could be included, including ultrasound, angiography, nuclear medicine, radiography, endoscopy, pathology, dermatology, etc.

Also connected to the network 190 may be a Picture Archiving and Communications System (PACS) 136 and PACS workstation 138.

Also connected to the network 190 may be a User Profile Data 160. The user profile data 160 may include a database or other data structure that stores information such as interaction data, series view order, series importance, and/or other data associated with various users. In various embodiments, the user profile data 160 may reside within PACS System 136, reside within a server accessible on a LAN that is accessible to the information display computing device 150, and/or reside within a server that is located remote to the information display computing device 150 and accessible via the Internet. In other embodiments, user profile data 160 may reside locally, within information display computing device 150. Information may be stored in the user profile data 160 (and/or elsewhere) in any computer readable format such as a database, flat file, table, or XML file, and may be stored on any computer readable medium, such as volatile or non-volatile memory, compact disc, digital video disc, flash drive, or any other tangible medium.

The PACS System 136 is typically used for the storage, retrieval, distribution and presentation of images (such as those created and/or generated by the MRI scanner 120 and CT Scanner 122). The medical images may be stored in an independent format, an open source format, or some other proprietary format. The most common format for image storage in the PACS system is the Digital Imaging and Communications in Medicine (DICOM) format. The stored images may be transmitted digitally via the PACS system, often reducing or eliminating the need for manually creating, filing, or transporting film jackets.

The network 190 may also be connected to a Radiology Information System (RIS) 140. The radiology information system 140 is typically a computerized data storage system that is used by radiology departments to store, manipulate and distribute patient radiological information.

Also attached to the network 190 may be an Electronic Medical Record (EMR) system 142. The EMR system 142 may be configured to store and make accessible to a plurality of medical practitioners computerized medical records. Also attached to the network 190 may be a Laboratory Information System 144. Laboratory Information System 144 is typically a software system which stores information created or generated by clinical laboratories. Also attached to the network 190 may be a Digital Pathology System 146 used to digitally manage and store information related to medical pathology.

Also attached to the network 190 may be a Computer Aided Diagnosis System (CAD) 148 used to analyze images. In one embodiment, the CAD 148 functionality may reside in a computing device separate from information display computing device 150 while in another embodiment the CAD 148 functionality may reside within information display computing device 150.

Also attached to the network 190 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D Processing functionality may reside in a computing device separate from information display computing device 150 while in another embodiment the 3D Processing functionality may reside within information display computing device 150

In other embodiments, other computing devices that store, provide, acquire, and/or otherwise manipulate medical data may also be coupled to the network 190 and may be in communication with one or more of the devices illustrated in FIG. 1, such as with the information display computing device 150.

As will be discussed in detail below, the information display computing device 150 may be configured to interface with various networked computing devices in order to provide efficient and useful review of medical examination data that is stored among the various systems present in the network. In other embodiments, information display computing device 150 may be used to display non-medical information.

Depending on the embodiment, the other devices illustrated in FIG. 1 may include some or all of the same components discussed above with reference to the Information Display Computer Device 150.

Figure 2:
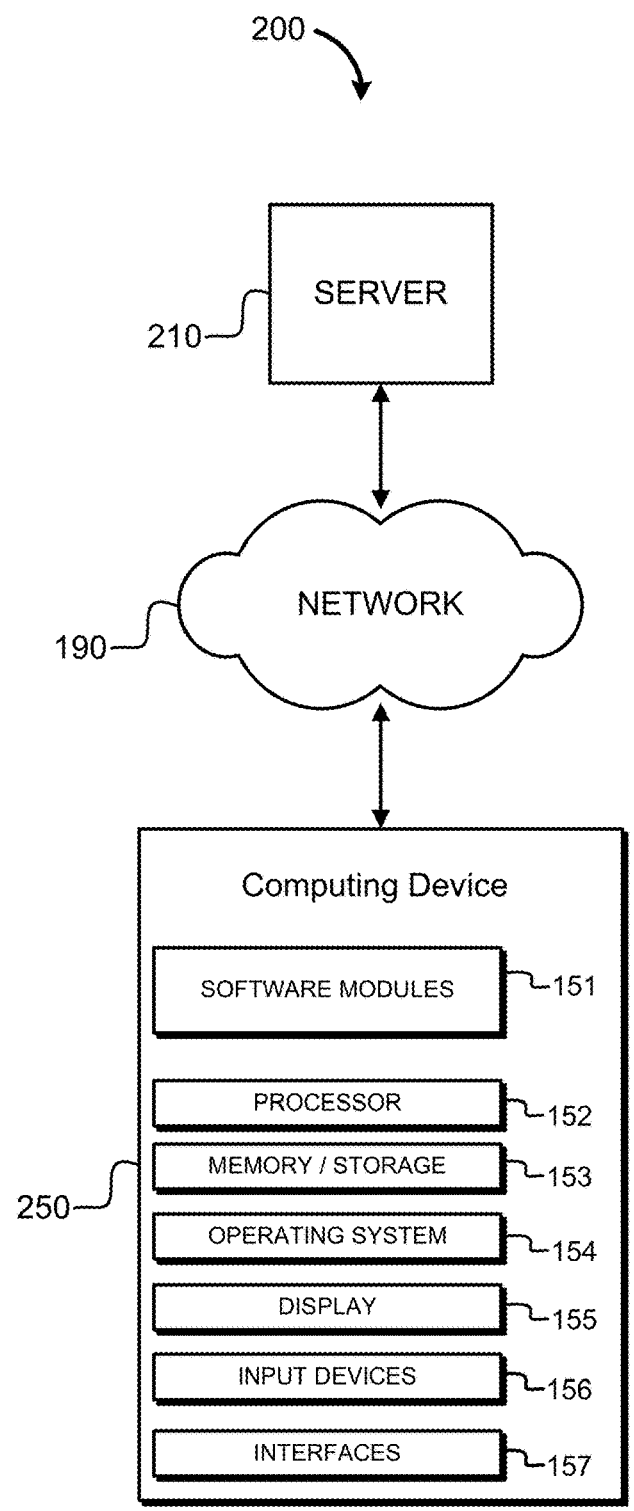
FIG. 2 is a system diagram which shows various components of a system for managing data (e.g., medical or non-medical data) utilizing certain systems and methods described herein.

FIG. 2 is a system diagram which shows the various components of a system 200 for managing data (e.g., medical or non-medical data) utilizing certain systems and methods described herein. As shown, the system 200 may include a computing device 250 and may include other systems, including those shown in FIG. 2.

The computing device 250 may take various forms. In one embodiment, the computing device 250 may be a computer workstation having software modules 151. In other embodiments, software modules 151 may reside on another computing device, such as a web server, and the user directly interacts with a second computing device that is connected to the web server via a computer network. The software modules 151 will be described in detail below.

In one embodiment, the computing device 250 comprises a server, a desktop computer, a workstation, a laptop computer, a mobile computer, a Smartphone, a tablet computer (e.g., the tablet computer 320 of FIG. 3), a cell phone (e.g., the smartphone 330 of FIG. 3), a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The computing device 250 may run an off-the-shelf operating system 154 such as a Windows, Linux, MacOS, Android, or iOS. The computing device 250 may also run a more specialized operating system which may be designed for the specific tasks performed by the computing device 250.

As with computing device 150 described herein with reference to FIG. 1, computing device 250 may include one more computing processors 152, may include memory storage 153, may include or be interfaced to one more display devices 155, may include or be interfaced to one or more input devices 156, and may include one or more interfaces 157.

Computing device 250 may communicate and/or interface with other systems and/or devices via network 190, as described herein with reference to FIG. 1.

Also connected to Network 190 may be a Server 210 that communicates with Computing Device 250, for example allowing communication of images or other data between Server 210 and Computing Device 250.

Example Computing Devices

Figure 3:
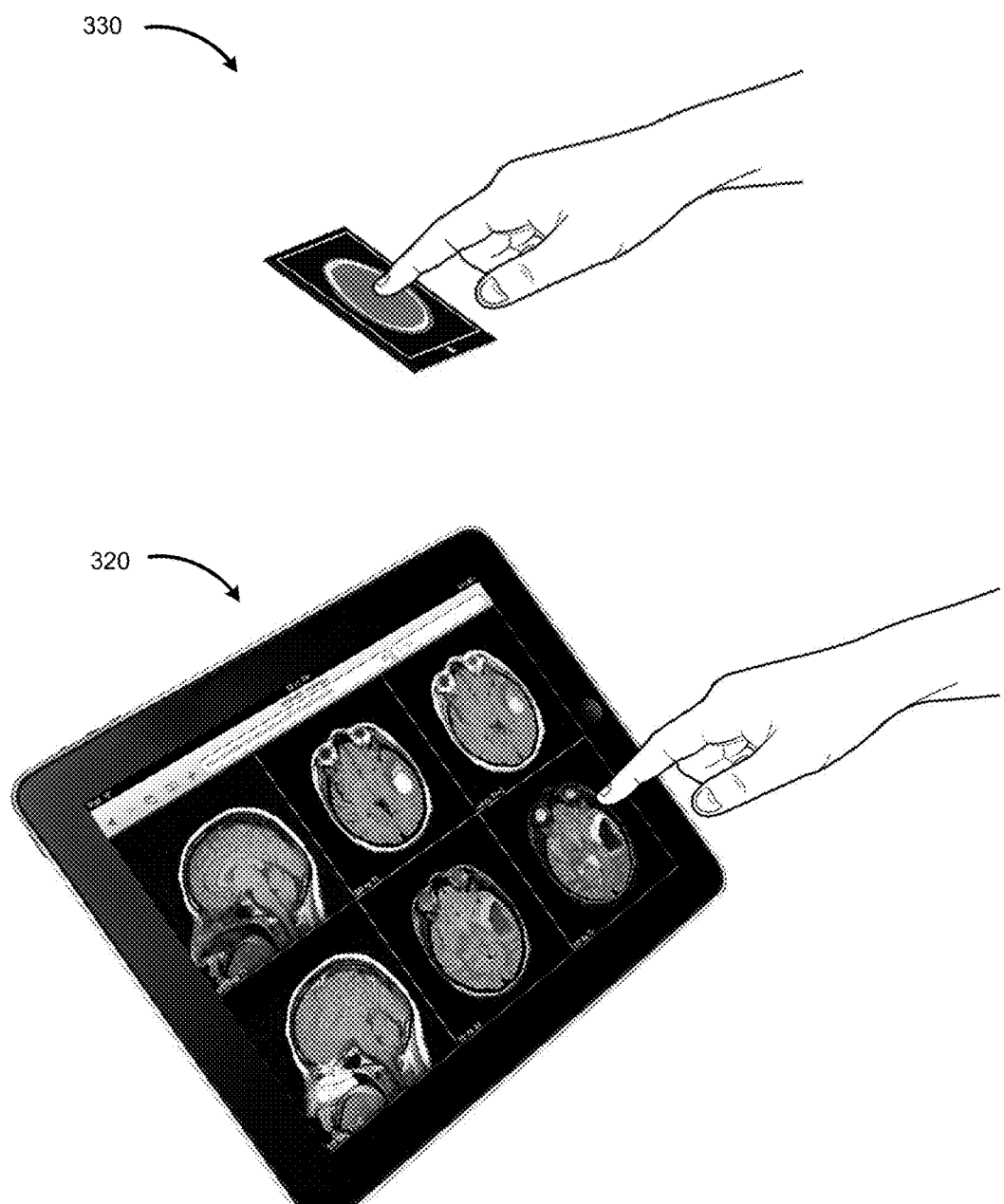
FIG. 3 illustrates example computing devices that may be used to perform various processes discussed herein.

FIG. 3 illustrates example computing devices that may be used to perform various processes discussed herein. For example, the computing device 150 or 250 could include the smartphone 330 or tablet computer 320 of FIG. 3. As discussed above, the system and methods described herein may be implemented on any other suitable computing device, such as those listed above.

Example Interaction Data

Radiologists and other physicians may prefer to view series in different orders based on clinical information. For example, radiologists and other physicians may prefer to first view series that they feel are most likely to demonstrate abnormalities for the given clinical indication. For example, in a patient suspected of having had an acute infarct, users may prefer to view the diffusion series first as it is most sensitive for detection of acute infarcts. Described below are systems and methods for using interaction data of users in order to optimize an order of transmitting, processing, and or presenting image series to a user.

Figure 4A:
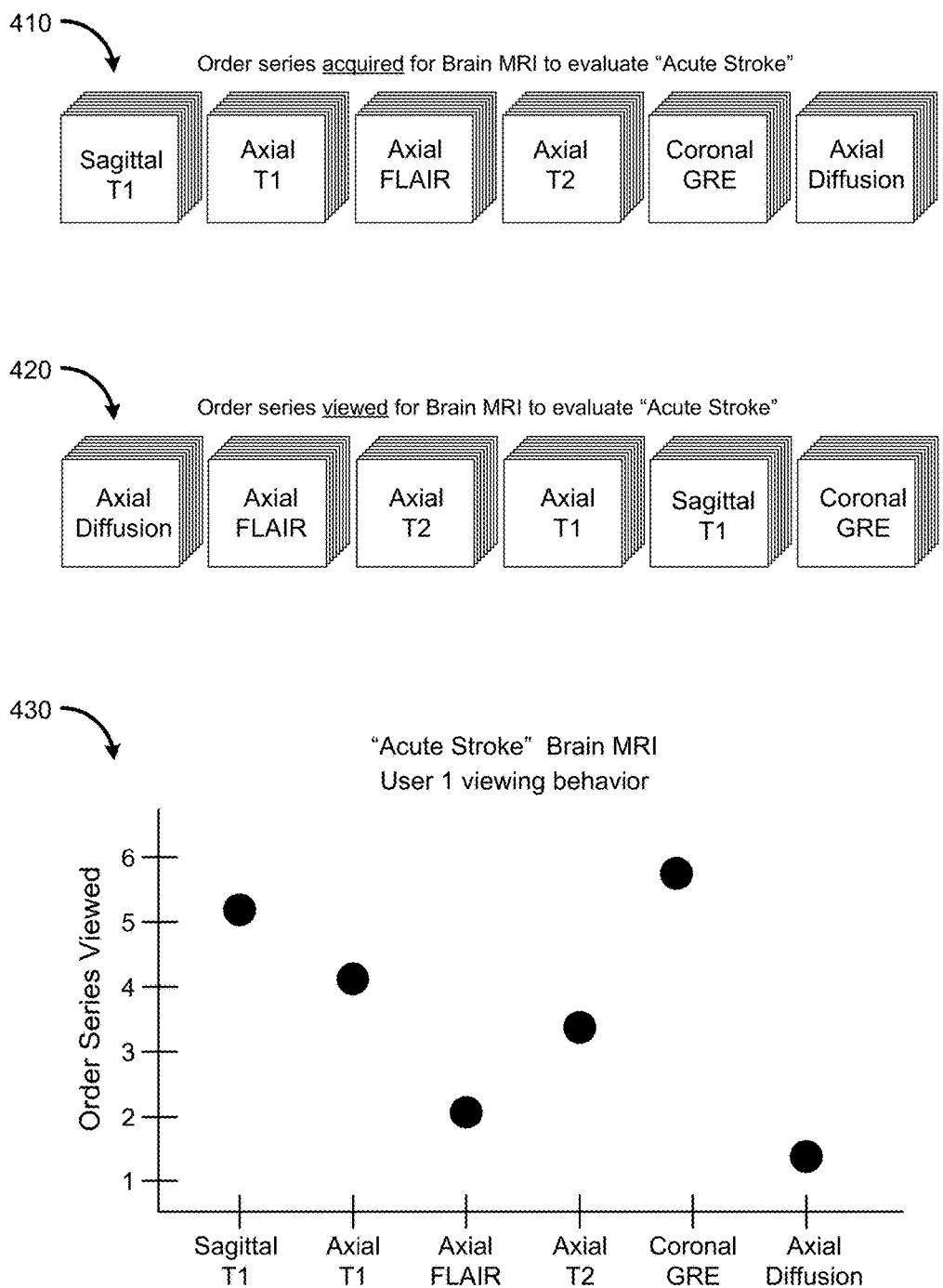

FIG. 4*a* illustrates example arrangements of image series of an exam, in particular, a brain MRI in the example of FIG. 4A. Arrangement 410 illustrates an order in which series of the example brain MRI were acquired, while arrangement 420 indicates an order in which the various series of the brain MRI were actually viewed by a particular user, user 1 in this example. Thus, arrangement 410 indicates that the Sagittal T1 series was acquired first, followed by Axial T1, Axial FLAIR, etc. In one embodiment, the order that series are acquired may be arbitrary and may vary from site to site and scanner to scanner. However, in some cases certain series are acquired in a particular order, e.g., if pre- and post-contrast images are acquired, the pre-contrast scans would be acquired before post-contrast scans.

As shown in arrangement 420, the order in which user 1 actually views the various image series differs from the order in which the series were acquired (arrangement 410). In particular, arrangement 420 indicates that the axial diffusion series was the first viewed series, followed by the Axial FLAIR, Axial T2, etc. Thus, the series view order, e.g., the way the viewer navigates through the images in a medical imaging exam, may differ among individuals, and may vary among a single user in view of other factors, such as clinical information associated with the images and/or factors related to the particular computing device on which the user is viewing the medical data.

As will be discussed with regard to different embodiments herein, it is useful for the device to know the likely order that the user will view the series.

FIG. 4a also illustrates a graph 430 that shows example interaction data that may be collected based on a user's behavior in viewing brain MRI exams associated with the clinical information "Acute Stroke", such as the series depicted in arrangements 410 and 420. Graph 430 illustrates an order in which the respective series of the brain MRI exams were viewed by the user, for example based on interaction data associated with the user viewing one or more exams previously. Thus, the graph 430 matches the order illustrated in arrangement 420 indicating that the Axial Diffusion series was the first series displayed, the Axial FLAIR series was second, etc. This viewing order may be used to automatically determine, on average, a user's preferred series viewing order, in this example for a Brain MRI performed with the clinical indication of "Acute Stroke." Accordingly, by collecting this interaction data (e.g., along with various other types of interaction data), as users view exams, a database of preferred series view order may be acquired, an example of machine learning. This data may then be used to predict the preferred series view order for the user as a function of modality, clinical indication, and/or other exam or user characteristics, when the user begins viewing an exam of the same (or similar) modality and/or clinical indication.

In this example, the clinical indication in the brain MRI is "Acute Stroke," but a similar or identical series might be obtained for many other clinical indications.

Figure 4B:
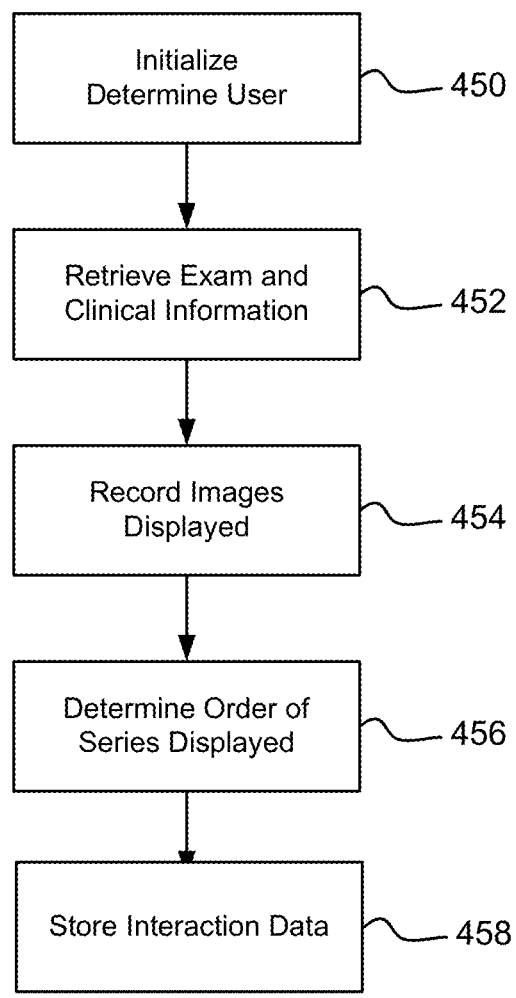
FIG. 4b is a flowchart illustrating one embodiment of a method of monitoring user behavior to collect interaction data, such as series views order.

FIG. 4b is a flowchart illustrating one embodiment of a method of monitoring user behavior to collect interaction data, such as series views order.

All flowcharts and/or methods discussed herein may include fewer or additional blocks and/or the blocks may be performed in a different order than is illustrated. Software code configured for execution on a computing device in order to perform the methods may be provided on a computer readable medium, such as a compact disc, digital video disc, flash drive, hard drive, memory device or any other tangible medium. Such software code may be stored, partially or fully, on a memory device of the computer, such as the computing device 150, computing device 250, and/or any other suitable computing device, in order to perform the methods outlined in the various flowcharts. For ease of explanation, the methods will be described herein as performed by a computing device 150 (which refers to either or both of the information display computing device 150 or 250); however, the methods may be performed by any other suitable computing device.

Beginning in block 450, the computing device determines an identity of the current user so that the interaction data that is captured can be associated with the particular user. In some embodiments, information is acquired anonymously or associated with a user group rather than (or in addition to) an individual user.

In block 452, exam information, such as the modality and series information, and clinical information associated with the exam and/or patient may be acquired, such as the clinical indication for the exam. In other embodiments, other clinical information may be utilized, such as the patient's past medical history, risk factors, etc. In other embodiments, other information, such as exam type and/or information from prior exams, may be utilized instead of, or in addition, to clinical information. Additionally, information regarding the user and/or the user's viewing environment (e.g., the type of device the user is viewing the images on) may be acquired.

In block 454, interaction data based on the user's behavior as he views the medical imaging exam (e.g., navigates between images of various series), is recorded. The interaction data may include the series type associated with each image that is displayed, length of time each image is displayed, user interactions with the image (e.g., resizing, zooming, changing widow levels, cropping, etc.), notations or tags associated with the image, previous and/or next images viewed, images and series displayed from other exams such as prior comparison exams, and/or any other information associated with the user's interaction with the image.

In block 456, the interaction data is analyzed to determine the series view order. In other embodiments, other characteristics of the user's viewing behavior may be determined based on the interaction data.

In block 458, the interaction data, including the determined order series view order, is stored, such as in the user profile data 160 (FIG. 1). In one embodiment, a series view order may be generated based on the user's viewing behavior for all exams of a certain type, such as a brain MRI. In another embodiment, a series view order may be generated for exams of a certain type coupled with clinical information, such as a brain MRI performed to evaluate for possible "acute infarction." In another embodiment, a series view order may be created by combining information from multiple users. Thus, a user may have multiple series view orders each associated with different combinations of clinical indications, modalities, display devices, etc.

Figures 5A, 5B:
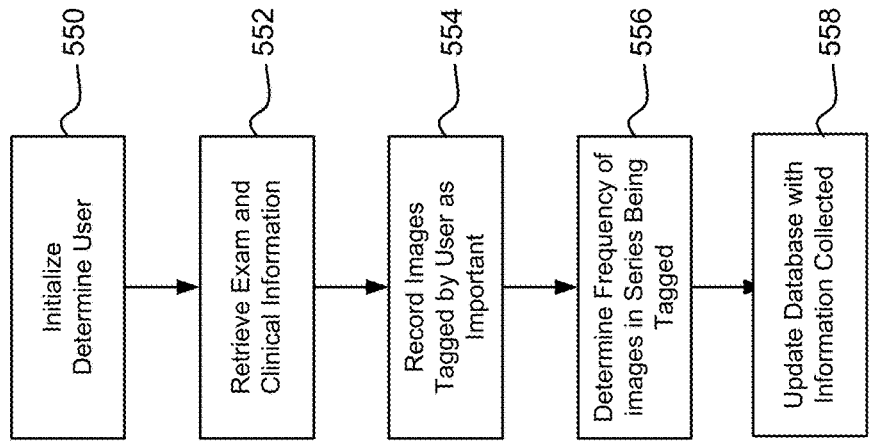
FIG. 5a is a table illustrating example series importance data that may be derived based on user interaction data (of a single or multiple users) in order to determine series importance as related to respective clinical indications.
FIG. 5b is a flowchart illustrating one embodiment of a method for monitoring user behavior to collect information related to series importance.

FIG. 5a is a table illustrating example series importance data that may be derived based on user interaction data (of a single or multiple users) in order to determine series importance as related to respective clinical indications. In the course of viewing exams, users may interact with the images to indicate images that are of particular interest. For example, a user may choose images to be marked as "key images" or placed in a "montage" of images that communicate the most important findings to other users, such as referring physicians that may later view the exam.

In some cases the images are chosen because they demonstrate an abnormality in the medical imaging exam, for example an enhancing mass. In other cases images are chosen because they show no abnormality, but the image is chosen from a series that the user feels would be the one most likely to demonstrate an abnormality if one existed. For example, in a patient imaged for suspected "Acute Stroke", a radiologist might tag a normal image from an "Axial Diffusion" series as a key image because that series might be the one expected to be most sensitive for detection of an acute infarct if one were present.

In the example table of FIG. 5a, the illustrated percentages indicate how commonly images of the respective series were marked as "key images" (and/or added to a montage) when associated with each of three example clinical indications. For example, FIG. 5a indicates that one or more image of the axial FLAIR series is marked as a key image 80% of the time when the clinical indication is Acute Stroke or Tumor Follow-up. However, one or more images of the axial FLAIR series is marked as a key image 95% of the time when the clinical indication is Multiple Sclerosis. Thus, while the Axial FLAIR series is important in each of the three example clinical indications, that series may be most important in the Multiple Sclerosis clinical indication. In the example of FIG. 5A, in the case of Acute Stroke clinical indication, the Axial Diffusion series was the most common series with images marked as key and/or added to a montage, followed by the Axial Flair series and Coronal GRE series. In the case of Multiple Sclerosis, the Axial Flair series was the most common series having one or more images marked as key and/or added to a montage, followed by the Sagittal FLAIR series and Axial T1+C series. In the case of Tumor Follow-up, the Axial T1+C series was the most common series having one or more images marked as key and/or added to a montage, followed by the Axial FLAIR series, Coronal T1+C and Sagittal T1+C Series.

Depending on the embodiment, the series importance (e.g. the percentages illustrated in FIG. 5A) may be determined based on interaction data of a single user or a group of users. In some embodiments, the user can provide a preference for which interaction data (e.g., user-specific or group) is used in determining series importance for that user, and may furthermore indicate a desired weighting of different sources of interaction data. For example, a user that is relatively inexperienced with viewing images associated with a particular clinical indication may wish to have series importance determined entirely (or primarily) based on interaction data of other users, for example a group of expert users. However, a user that is very experienced with viewing images associated with a particular clinical indication may wish to have series importance determined solely (or mostly) based on interaction data of the user himself.

In other embodiments, rather than a percentage indicator of how frequently images of respective series are marked as key images and/or placed in a montage (as discussed above), a scoring algorithm or model that considers other factors may be used to rank relative importance of series. For example, a scoring model may consider a quantity of images of a particular series that are marked as key images and/or placed in a montage in generating an "importance score" for that particular series. Thus, for a particular exam type (or exam type with a particular clinical indication or having other particular clinical information), series of the exam may each have an importance score that is based on the quantity of images of respective series that are marked as key images and/or added to a montage, for example. In some embodiments, different weightings are assigned to image series based on whether images were marked as key images or images were placed in a montage. For example, a series having one image added to a montage may have a different importance score (either higher or lower depending on the particular scoring algorithm) than a series having one image that was marked as a key image.

In some embodiments, importance scores may be determined based on characteristics of users from which interaction data was acquired. For example, a first user that is an expert in a particular area (e.g., in interpreting brain MRIs) may have his actions with reference to exams in that particular area (e.g., his actions in marking images of brain MRIs as key images and/or adding brain MRI images to montages) weighted much higher than a user that is relatively inexperienced at reviewing exams in that particular area (e.g., a user that rarely reviews brain MRIs). Thus, importance scores may more closely approximate preferences and knowledge of experts in a particular area (or some other group of individuals that are designated to have a higher weighting, such as individuals within a particular radiology group of a user) without being skewed by non-experts (or users outside of the particular radiology group of the user). Additionally, other aspects of the user's behavior with reference to images of respective exam series (including those discussed in the following paragraph) may be included as factors in an importance scoring algorithm.

A number of aspects of the user's behavior may be used to determine which series are important, and this information may be correlated to various clinical indications (and/or other characteristics of an exam). For example, one or more of the following may be used to rank various series in terms of importance:
  Order in which various series are viewed by the user
  Frequency that images for a series type are used for measurements
  Frequency that images for a series type are selected by the user for various operations, for example,
    Selected as a "key image"
    Selected for inclusion in a montage of images selected to summarize the results of the exam
    Selected for inclusion in a report.

Once the series importance of various series of an exam is determined, the information could be used to increase efficiency of a viewing user in a number of ways. For example, the series importance data (e.g., series importance scores calculated based on one or more of the characteristics listed above) may be used to direct the user's attention first to a series having a highest series importance. Depending on the embodiment, one or more of the following could be used to communicate the series importance of series to the user:
  Importance could be used to determine the order series are presented to a user.
  Importance could be used to determine an order in which series are transmitted to a user, such as from an imaging center to a radiologist's viewing device.
  Particularly important series could be pointed out to users by highlighting them on a list or visually distinguishing them on a computer display.
  Series that are ranked low might be candidates for series that might be eliminated from imaging protocols, reducing scan time, or might be placed last in a hanging protocol used by particular users.

In some embodiments, the series importance data may be used as part of a cognitive augmentation application wherein such series importance data provides user feedback (e.g., akin to user voting) by one or more user as to the importance, sensitivity and/or relevance of various series in various clinical indications.

FIG. 5b is a flowchart illustrating one embodiment of a method for monitoring user behavior to collect information related to series importance.

Beginning in block 550, the computing devices determines the user's identify so the behavior monitored can be associated with the user. In some embodiments, interaction data is acquired anonymously or associated with a user group rather than an individual user.

In block 552, clinical information associated with the exam may be acquired, such as the clinical indication for the exam. In some embodiments, other clinical information may be utilized, such as the clinical indication, patient's past medical history, risk factors, etc. In other embodiments, other information, such as exam type, may be utilized instead of or in addition to clinical information. Additionally, information regarding the user and/or the user's viewing environment (e.g., the type of device the user is viewing the images on) may be acquired.

In block 554, interaction data based on the user's behavior as the user views the medical imaging exam is recorded. For example, the interaction data may monitor and include indications of images that the user selects as "important." In different embodiments, an image series may be marked as "important" if the user does one or more of the following:
  Selects one or more images of the series to be flagged as a "key image," which may indicate that the image series is clinically important, for example using information recorded in DICOM data.

Selects one or more images of the image series to be included in a "montage" of images that is stored with the exam for the purpose of communicating relevant findings to other uses that may view the exam.

Performs an operation on one or more images of the image series, e.g. makes a measurement and/or processes one or more images, for example using multiplanar reformatting, 3D volume rendering, and/or Computer Aided Diagnosis software.

Manually marks one or more images of the series or the entire series as one that should be considered important for purposes of determining series importance.

Depending on the embodiment, a threshold quantity of images of a series that are required to meet one or more of the criteria above may be set, such as based on user, system, site, or default software preferences. For example, one embodiment may require only one image of a series to be flagged as a key image for the series to be marked as important (e.g., a user may set a threshold to one), while another embodiment may require two or more images of a series to be flagged as key images for the series to be marked as important (e.g., a user may set a threshold to two).

Moving to block 556, the interaction data, such as the information discussed with reference to block 554, is analyzed to determine the frequency that images of a series type is tagged as important, for example, where the number of images tagged within each series weights the importance of the series.

In block 558, the interaction data, including the determined series importance data, is stored for use in customizing the user's experience with similar exams in the future. In one embodiment, series importance data may be generated based on the user's viewing behavior for all exams of a certain type, such as a brain MRI. In another embodiment, series importance data may be generated for exams of a certain type coupled with clinical information, such as a brain MRI performed to evaluate for possible "acute infarction". In another embodiment, series importance data may be created by combining information from multiple users. Thus, in some embodiments blocks 556 and 558 are performed periodically, rather than each time new interaction data is acquired.

In some embodiments, importance of individual images may be tracked in addition to, or as an alternative to, tracking importance of series of images. For example, a particular image of a brain MRI may have a high importance score in view of the user marking images of that particular anatomy as important in multiple previous exams (relative to a frequency of the user marking images of other anatomy as important in the same multiple previous exams). Thus, in one embodiment a computing system may determine an order of display of images of a particular series (or of multiple series) based on relative image importance data. Similarly, in some embodiments importance of sections of images within image series may be tracked. For example, a brain MRI image series may have multiple different sections (e.g., five sections) each comprising multiple images. In one embodiment, importance scores may be generated for each of the different sections in order to allow later displays of similar exam series (e.g., from exams of the same type and/or having the same clinical indication and/or other clinical information) to be optimized by ordering display of exam sections based on the relative section importance scores. In embodiments where importance scores for individual images and/or sections of image series are tracked, the system may include registration algorithms that match the anatomy of images (or sections of images within a series) for compilation of importance scores for particular images or image sections and for display of appropriate corresponding anatomy based on stored importance scores.

Figure 6:
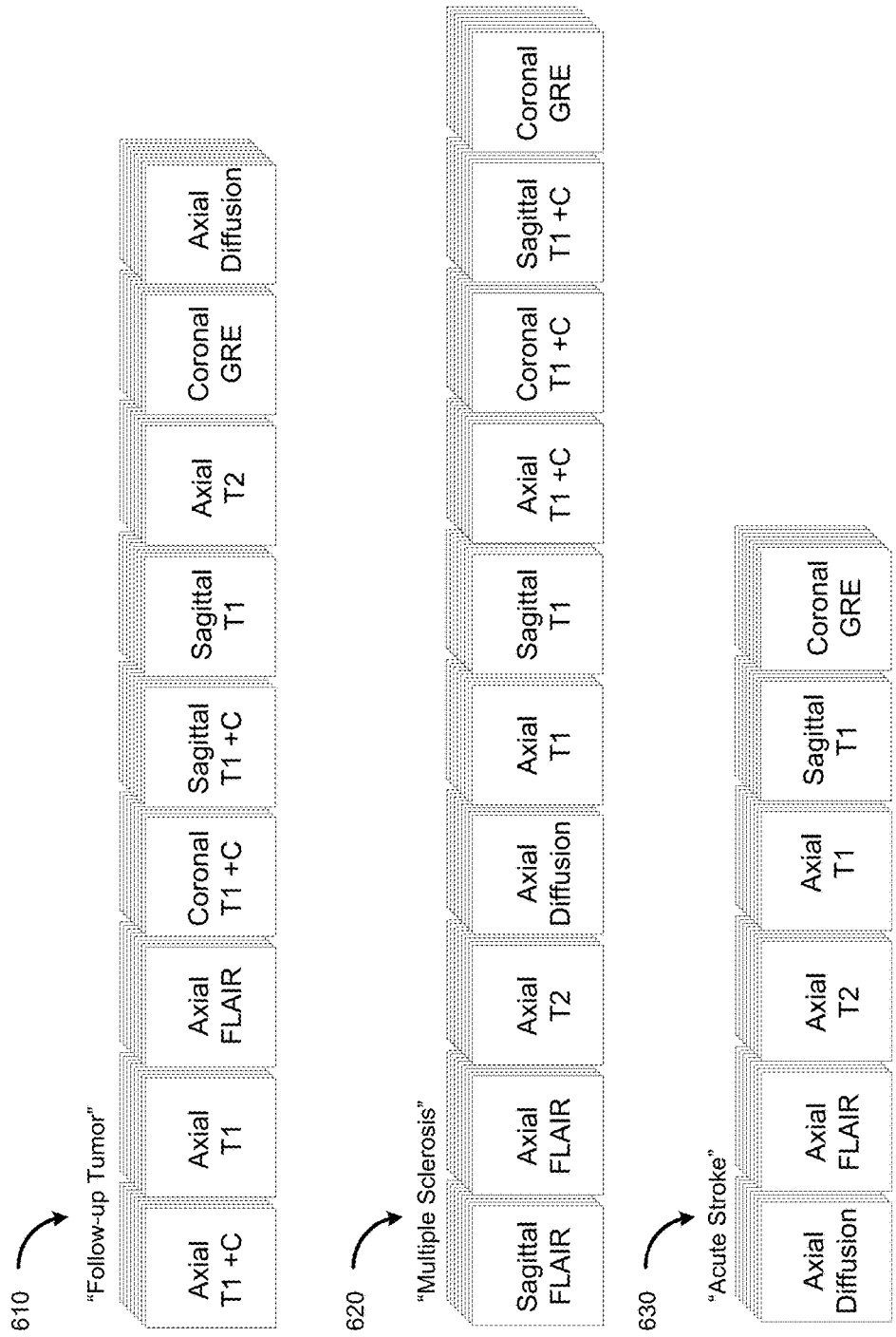
FIG. 6 illustrates exemplary orderings of series based on series importance for the respective exam indication.

FIG. 6 illustrates exemplary orderings of series based on series importance for the respective exam indication. In particular, FIG. 6 illustrates a "Follow-up Tumor" series importance order 610 indicating that the Axial T1+C series was found to be the most "important" series based on user interaction data, followed by the "Axial T1" series, etc. As noted above, depending on the embodiment, series importance may be based on interaction data for a particular user and/or a group of users.

In this example, the "Multiple Sclerosis" series importance order 620 indicates that the "Sagittal FLAIR" series was found to be most "important", followed by the "Axial FLAIR" series, etc. In this example, the "Acute Stroke" series importance order 630 indicates that the "Axial Diffusion" series was found to be most "important", followed by the "Axial FLAIR" series, etc.

Because series importance may be customized based on the particular user(s) interaction data that is used in developing the series importance, different users may have different series importance for the same exam type and clinical indication. Furthermore, series importance may change over time as additional user interaction data is obtained and used in determining series importance for a particular user.

Figure 7:
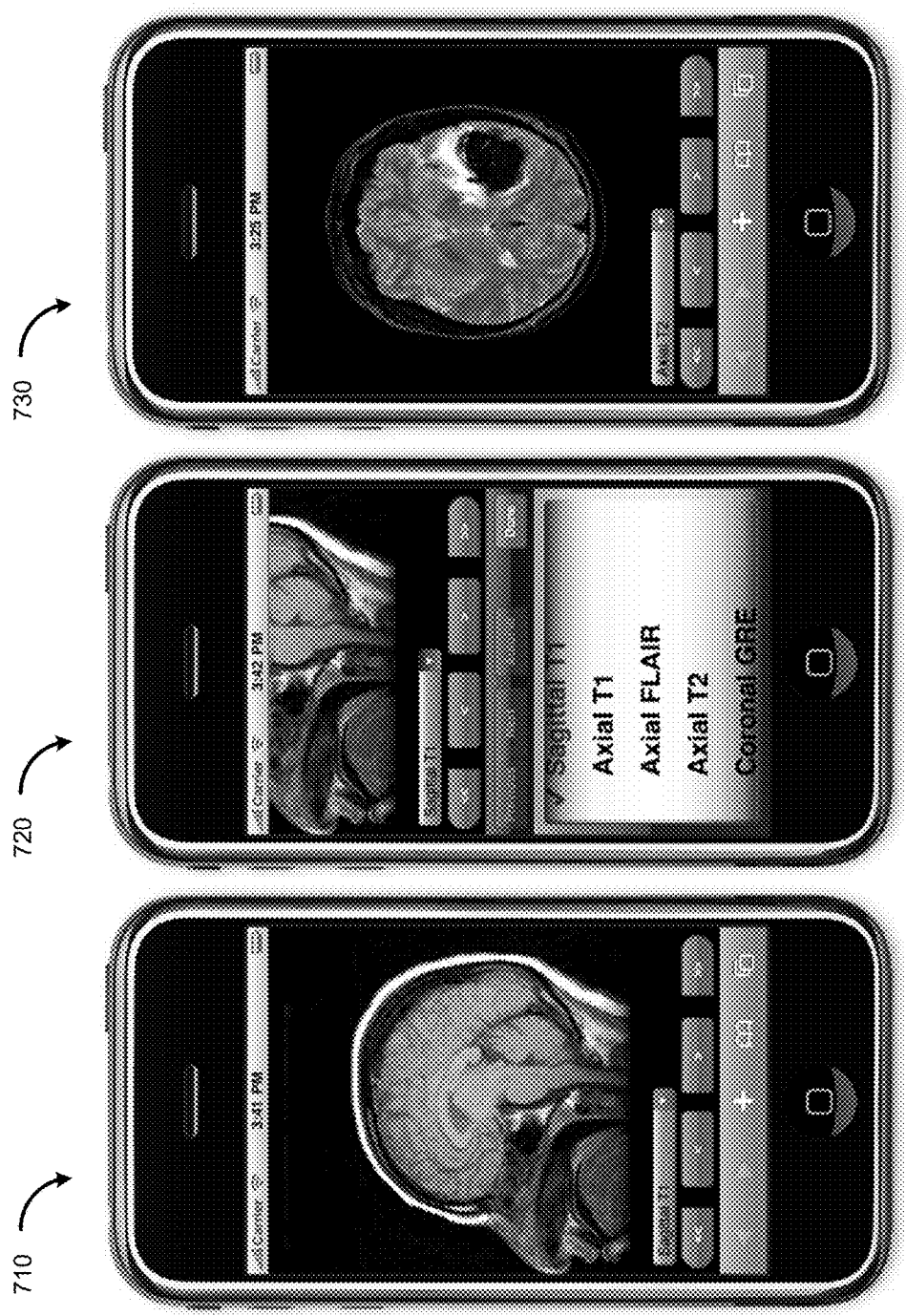
FIG. 7 illustrates a computing device as images are selected and displayed on a computing device.

FIG. 7 illustrates a computing device as images are selected and displayed on a computing device. In particular, view 710 illustrates a mobile computing device displaying an image from a brain MRI. In this example, the device is displaying an image from the first series acquired.

In various embodiments, different methods may be used to allow the user to select other series for display as well as select different images within the series to display. For example, as shown in view 720, a drop down list may be used to select a series to display. The example drop down list shown has "Sagittal T1" selected. View 720 illustrates a list of series available for display and allows the user to select another series, for example the "Axial T2" series, which would result in the display of that series.

View 730 illustrates the display after the user has selected the axial T2 series for display, such as by using the drop-down list illustrated in 720. In this embodiment, if the user were viewing an exam for "Acute Stroke" and desired, for example, to routinely view the Axial Diffusion series first, the system would be inefficient because the user would need to perform the following steps:

Select the drop down menu to display the list of the various series

Find the Axial Diffusion series within the list. In the example illustrated the user would need to scroll the list to find that entry as it is below the entries listed.

Select "Axial Diffusion" from the list.

In other embodiments, buttons may be utilized rather than the drop down menu. In the example shown, the buttons labeled ">>" and "<<" may be used to display the next or prior series, respectively. The buttons labeled ">" and "<" may be used to display the next or prior image within a series. In other embodiments, touch actions, such as left and right finger swipes to advance to the adjacent series, may be utilized to change series and images within series. However, use of the buttons and/or touch actions to navigate between image series that are stored in the original acquisition order or in alphabetical order introduces similar inefficiencies as use of the drop-down list. For example, if an image series that a user routinely prefers to view first is positioned near the end of a series list, the user may have to push the series advanced button multiple times, each time checking to see which series is display, in order to get to the desired series.

Example Applications of Series View Order and Series Importance

More efficient methods for allowing the user to quickly and easily view image series of most importance are discussed below.

Figure 8:
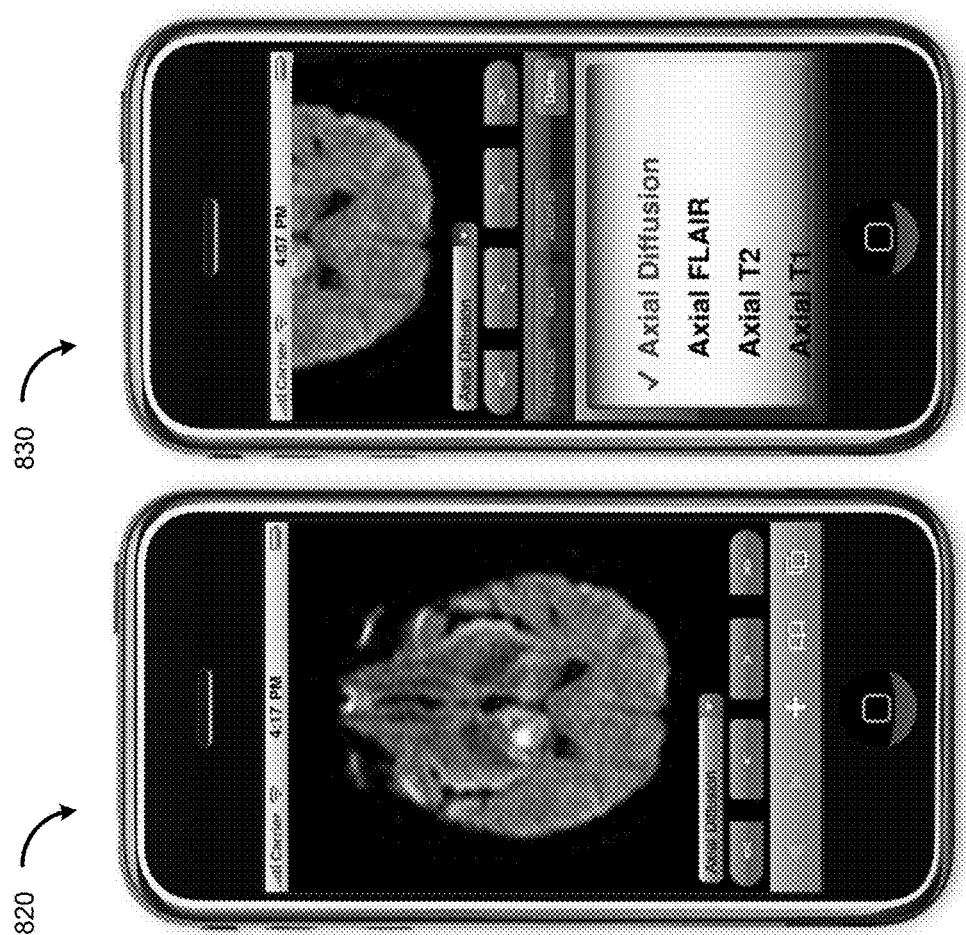
FIG. 8 illustrates a computing device as images are selected and displayed on the computing device.

FIG. 8 illustrates a computing device as images are selected and displayed on the computing device. In particular, view 820 of FIG. 8 illustrates the mobile computing device displaying an image from a brain MRI. In this embodiment, the series are ordered based on the user's typical or desired series view order. For example, the user's series view order may be determined based on stored interaction data associated with user, and also associated with the particular exam type and/or clinical indication. Thus, the order in which the user previously viewed series for the current clinical indication may be used in order to decrease navigation required by the user to view series of the newly selected exam in that same order.

In some embodiments, the series may be arranged in order of importance, based on the systems and methods described herein. For example, the device 820 may display an image from the image series having the highest series importance (rather than from the first series acquired as in FIG. 7). As discussed herein, the user's profile (and possibly interaction data of other users) may be used to determine series importance for various series associated with a particular clinical indication, in this case "Acute Stroke." Thus, the interaction data can be used to generate a custom order for presentation of image series that is different than the order acquired. For example, the series order for a brain MRI performed for "Acute Stroke" might be in the order shown in view 630 in FIG. 6. Therefore the first series displayed would be the "Axial Diffusion" series, as illustrated in view 820.

Using certain systems and methods described herein, view 830 illustrates the list of series that might be displayed on a handheld computing device if the user touched the drop down list. Note the order of the series listed is the same as shown in the example of view 630 of FIG. 6, which is a custom series ordering based on series importance data.

In some embodiments, the series order presented to a user may be determined based on a combination of series view order for the particular user as well as series importance data for the user (and possibly other users). Depending on the embodiment, the user may be able to customize the relative importance of having the series ordered based on series view order as opposed to series importance. For example, a first user may indicate that the series order for a particular exam type, with or without associated clinical information, should be based on primarily (e.g., 80%) on the users series view order, with some consideration (e.g., 20%) for series importance data from a group of specialists in the field. Likewise, a second user may indicate that the series order for the same exam type should be based on primarily (e.g., 75%) series importance data for the user, with some small consideration (e.g., 25%) for series view order for the user. Thus, the user is provided with various levels of customization to allow the computing device to intelligently determine a most appropriate ordering of series of an exam.

Figure 9:
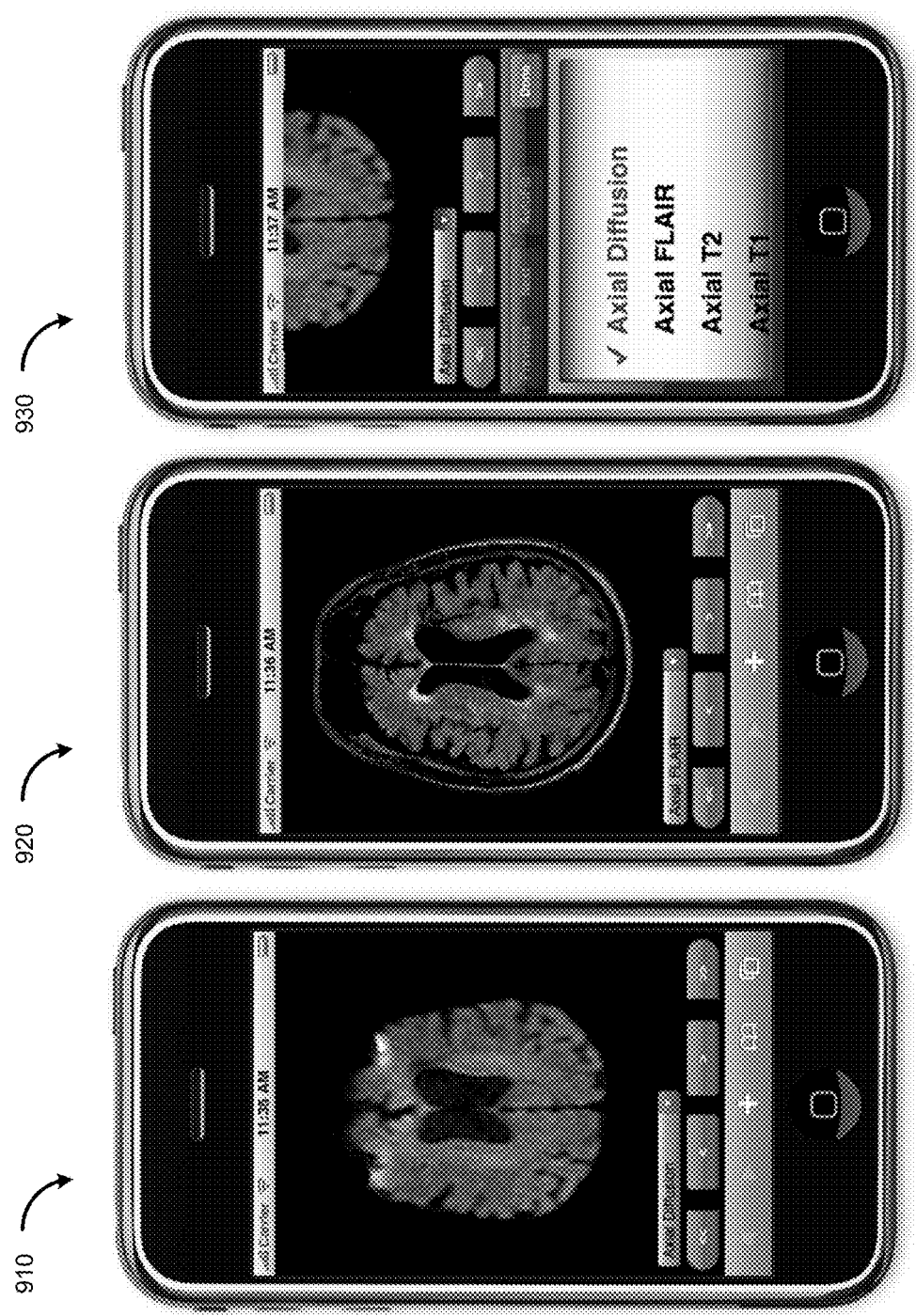
FIG. 9 illustrates additional views of the image series discussed with reference to FIGS. 7 and 8, again with the series ordered according to series view order and/or series importance, as discussed with reference to FIG. 8.

FIG. 9 illustrates additional views of the image series discussed with reference to FIGS. 7 and 8, again with the series ordered according to series view order and/or series importance, as discussed with reference to FIG. 8.

Figure 10:
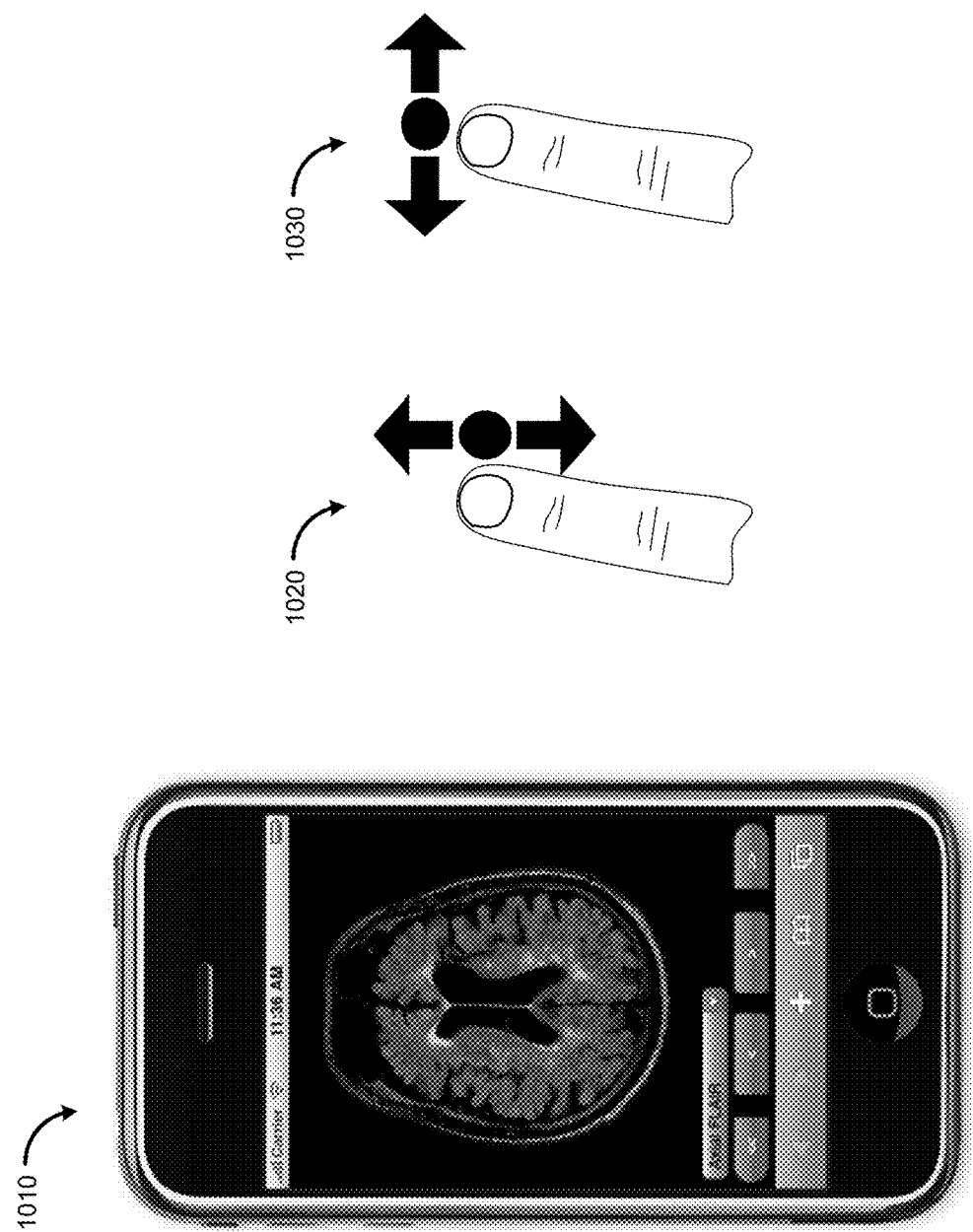
FIG. 10 illustrates an embodiment where the user may change series and images using touch gestures.

View 910 illustrates an image from the first series in the custom order illustrated in series importance order 630 (FIG. 6), the Axial Diffusion series. When the user is done viewing the images in that series, he may advance to the next series, for example by pressing a button, e.g., the one labeled ">>", or by a touch gesture, as illustrated in FIG. 10. View 920 illustrates the display of an image from the next series, the Axial FLAIR series.

This workflow allows the user to advance through the series, from most to least "important" without needing to display the list of series and manually select from the list. In another embodiment, the series may be listed in order of the user's preferred series view order as described herein.

View 930 illustrates the list of the various series, for example in response to the user selecting the drop down menu, ordered, for example, based on series view order or series importance, as described herein.

FIG. 10 illustrates an embodiment where the user may change series and images using touch gestures. View 1010 illustrates a device that includes a touch screen display. View 1020 illustrates gestures that a user might use to change the image displayed within a series. For example, touching the screen and moving the finger up might advance to the next image within a series, while touching the screen and moving the finger down might display the prior image in the series. View 1030 illustrates gestures that a user might use to change the series displayed within the exam. For example, touching the screen and moving the finger left might advance to the prior series, while touching the screen and moving the finger right might display the next series.

Figure 11:
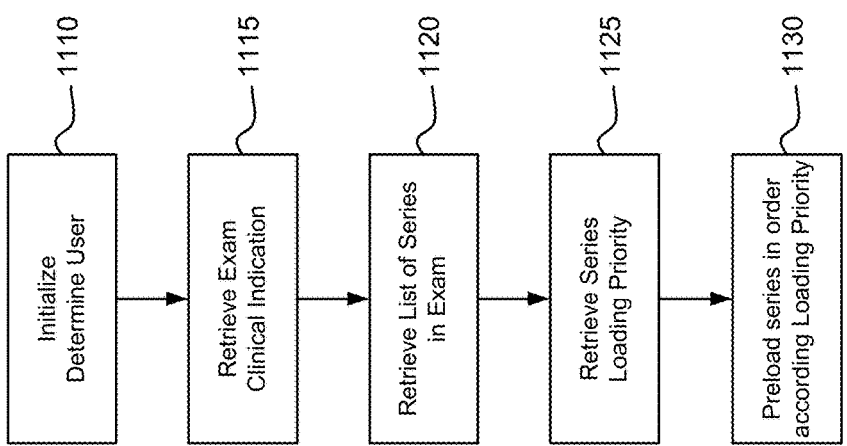
FIG. 11 is a flowchart illustrating one embodiment of a method of pre-loading series based on a custom series order, such as based on series view order of the user and/or series importance for various series.

FIG. 11 is a flowchart illustrating one embodiment of a method of pre-loading series based on a custom series order, such as based on series view order of the user and/or series importance for various series. In some scenarios, real-time communication of images to the computing device may be too slow to support the performance desired by the user, for example when image communication occurs over the internet or via cellular data networks. Preloading images into the memory of a display computing device or into relatively fast local storage may reduce and/or overcome this problem. This process may be optimized by preloading images in the order they are likely to be needed for display by the user, referred to here as the "Series Loading Priority." Based on systems and methods described herein, the series loading priority may be based on series view order, series importance, and/or set explicitly, for example as a user, group, or site preference.

Beginning in block 1110, the computing device determines the user and/or user group specific for which the exam is to be transferred. Depending on the embodiment, the preloading order may be determined by the actual display computing device (e.g., a radiologist's tablet) or by a network device, such as a PACS server or electronic medical records system, for example. Thus, discussion of processes performed by a computing device may refer to one or both of the client (e.g., the doctors computing device) or server (e.g., the image server).

In block 1115, clinical information associated with the exam may be acquired in embodiments where that information is used to determine the series loading priority, such as when series view order and/or series importance are associated with specific clinical information (e.g., clinical indication and/or exam type).

Next, in block 1120 the list of series associated with the exam is retrieved and in block 1125 the series loading priority is determined and/or retrieved, e.g., from the user profile data 160 of FIG. 1. In various embodiments the series loading priority may be based on information collected on the individual user or group of users. In other embodiments the series loading priority may be predefined for the user, user group, site and/or system preference.

In block 1130 the series are transferred to the computing device in an order based on the series loading priority, for example from a server to the user's computing device or LAN.

In another embodiment, the series loading priority is utilized to prioritize the order of a function other than transfer of series. For example, the series loading priority might be utilized to order processing of images prior to display, for example image decompression or creation of MPR (multiplanar reconstruction) images based on a user, user group, site, or system protocol for automatic generation of MPR or 3D volumetric rendered images.

Figure 12:
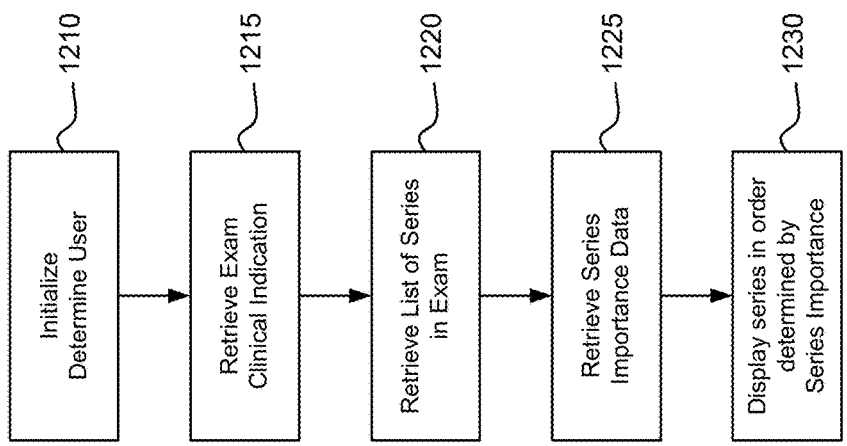
FIG. 12 is a flowchart illustrating one embodiment of the method of presenting series of an exam based on determined series importance.

FIG. 12 is a flowchart illustrating one embodiment of the method of presenting series of an exam based on determined series importance.

Beginning in block 1210, the computing device determines the user and/or user group specific to which the image series will be presented. As discussed above, the order of presenting image series of the exam may be customized based on preferences of the particular user and/or groups to which the user is a member.

In block 1215, clinical information associated with the exam may be acquired in embodiments where that information is used to determine the series importance.

In block 1220, the list of series associated with the exam is retrieved.

In block 1225, the series importance data is retrieved, for example from the User Profile Data 160 of FIG. 1. In various embodiments the series importance may be based on interaction data collected on the individual user or group of users. In other embodiments the series importance may be predefined for a user, user group, site and/or system preference.

In block 1230, the series are displayed by the computing device in an order or image configuration based on the series importance.

Figure 13:
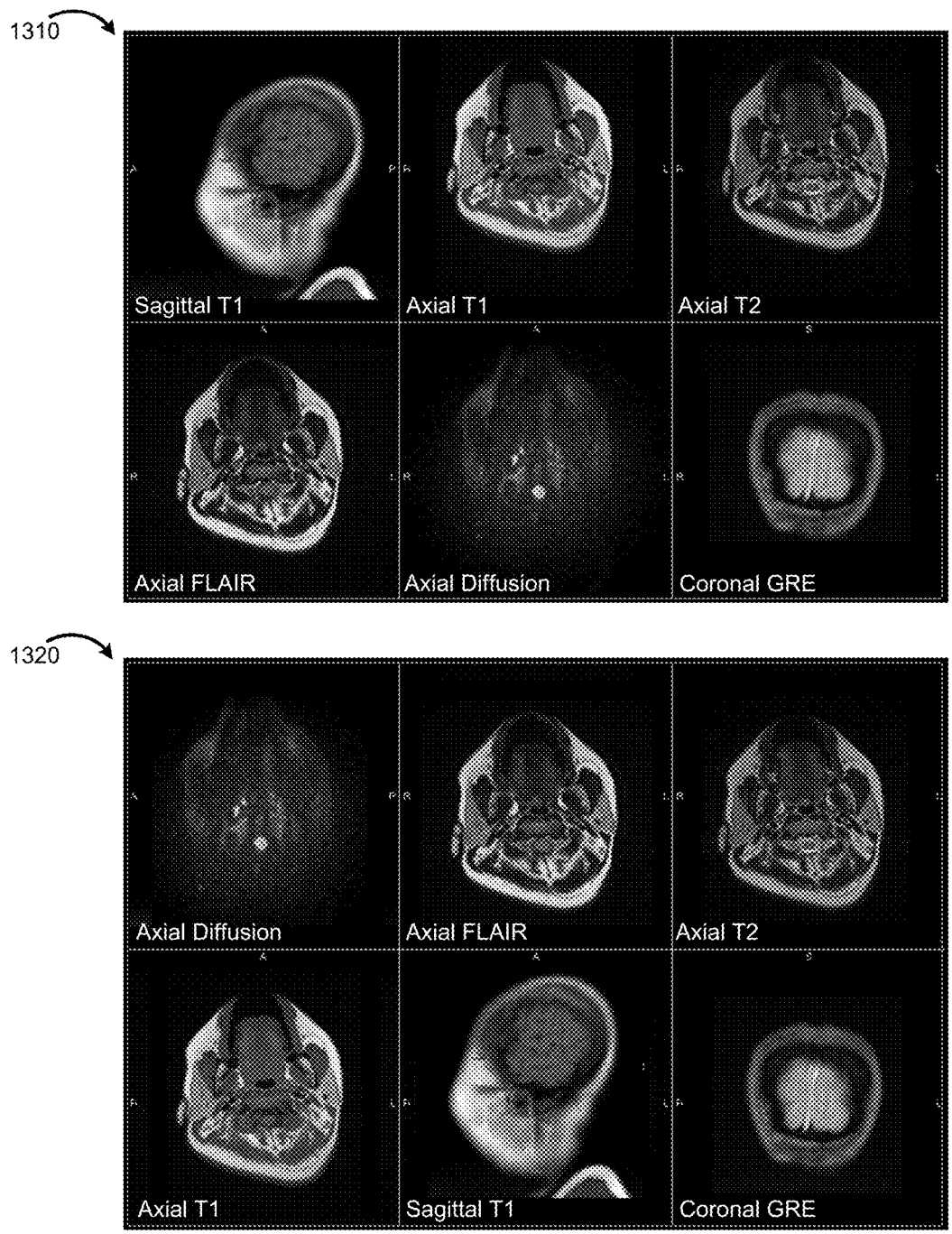
FIG. 13 illustrates an example screen from a computing device configured to display images from multiple image series concurrently.

FIG. 13 illustrates an example screen from a computing device configured to display images from multiple image series concurrently. In the example illustrated, six image frames are shown, each displaying a series from a medical imaging exam. In this example, the series are each from a brain MRI exam and the series types are indicated in the image frames, e.g., Sagittal T1, Axial T1, etc. Any number of image frames may be utilized and they may be displayed on one or more display devices. The operations described here could occur on any computing device, such as a PC, workstation, tablet computer, handheld device, etc. Within each frame the user may display other images within the associated series, for example by performing certain operations with a computer mouse such as holding down the left mouse button and moving the mouse up or down, by clicking on a button displayed on the computer screen (not shown), by pressing a key on a keyboard, via a gesture on a touch screen, etc.

The user is free to view the images within the frames in any order desired and change the series displayed in each frame, for example by rearranging the series displayed on the screen or displaying series that are not displayed, for example if there are more series than image frames.

The initial arrangement of series on the display may be determined by a hanging protocol, for example specific to the user, and the user may prefer the example shown in view 1310 for brain MRI exams, regardless of the clinical indication. However, based on the clinical information associated with the exam, the user may choose to review the various series in a different order depending on the clinical information associated with the exam.

When a radiologist or other user chooses a medical imaging exam to display on a computing device it may require a significant amount of time for the images associated with the exam to be transferred to the computing device, particularly if a slow network, internet, or cellular data network is utilized. The time required to transfer the information may result in user frustration and decreased efficiency as the user waits for the information to be transferred.

Using systems and methods described herein, the information that the user is likely to display first may be prioritized so that it is available first. For example, for a patient with a clinical history of "Acute Infarct," the user may prefer to view images in the Axial Diffusion series first because the user believes that the Axial Diffusion series is the most sensitive for detection of acute infarction. Based on systems and methods described herein, the system may be configured to load the Axial Diffusion series first so that it would be available for the particular user to view immediately. In contrast, when an exam is selected with a different clinical indication, such as "Follow-up Multiple Sclerosis," the user may prefer to view the "Sagittal FLAIR" images first, so that series would be given the highest priority.

It is noted that the series loading priority may be independent of the arrangement of the series on the display device, for example as determined by hanging protocols.

In other embodiments, the series view order and/or series importance data may be utilized to automatically control the arrangement of the series on the display device, such as by modifying or generating hanging protocols. This may provide cognitive support, for example to non-expert users. For example, the series importance data from a group of radiologists or other experts may be determined and used to customize the arrangement of series on the display device, such as by generating a customized hanging protocol for the particular clinical indication. For example, the series orders shown in FIG. 6 might represent the series importance information from a group of expert readers for brain MRI exams performed for three different clinical indications. View 1320 illustrates an example from an embodiment where the series are arranged on the display device according to their importance. In this example, a brain MRI was performed with the clinical indication of "Acute Stroke." As a result of the application of certain systems and methods described herein, the series are arranged in order of importance, from left to right and top to bottom. Specifically, the series order is Axial Diffusion, Axial FLAIR, Axial T2, Axial T1, Sagittal T1 and Coronal GRE, corresponding to the series order shown in view 630 of FIG. 6.

In some embodiments, the series loading priority (discussed with reference to FIG. 11) and the series importance data are both utilized in order to optimize the availability of the most important image series and arrange the image series in an order that highlights those of most importance.

In another embodiment, the arrangement of series on a display device, for example as discussed with reference to view 1320 above, is based on series view order rather than (or in combination with) series importance.

Figure 14:
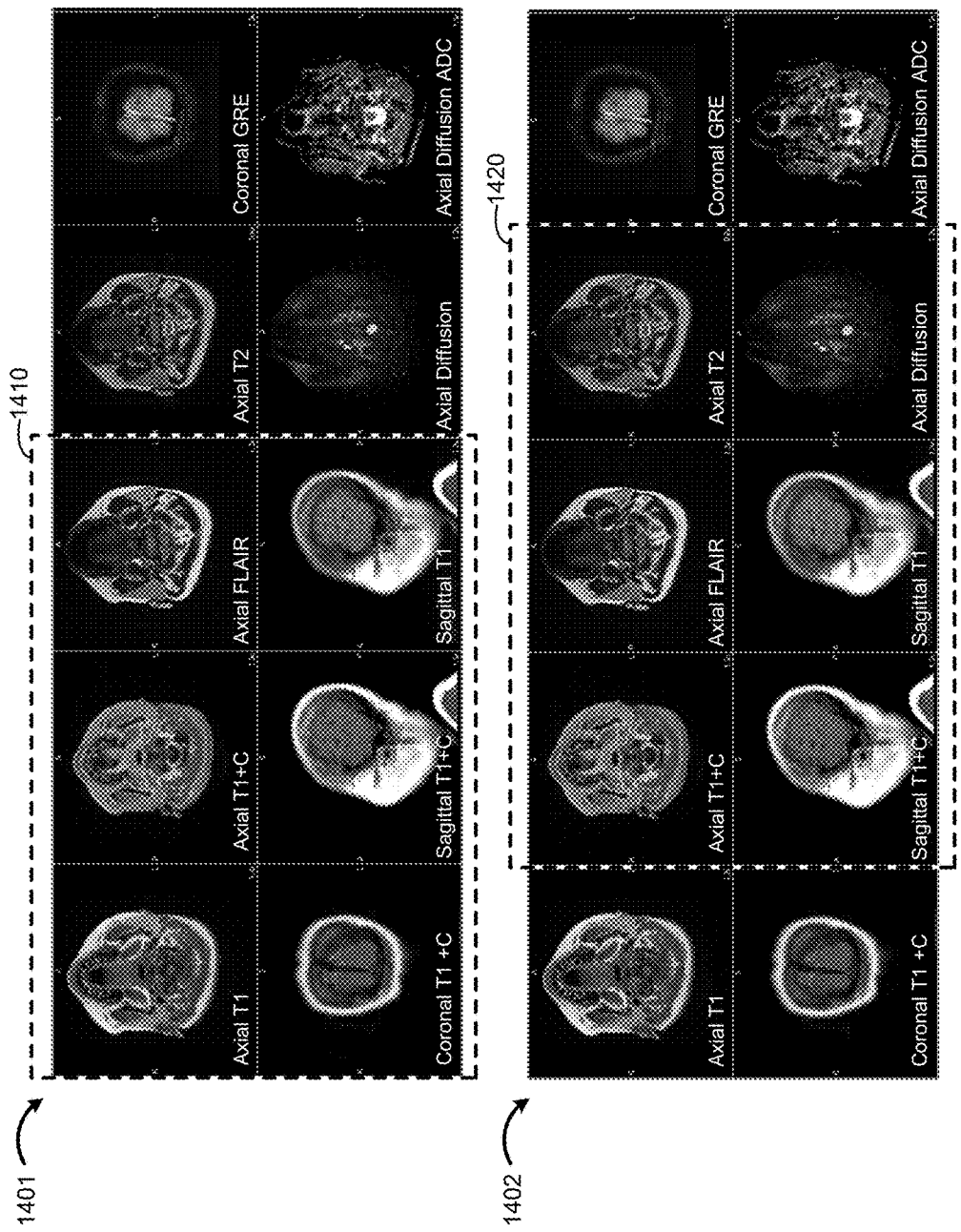
FIG. 14 illustrates an arrangement of various image series, wherein six of the image series may be displayed on a display device (or multiple display devices) concurrently.
Figure 15:
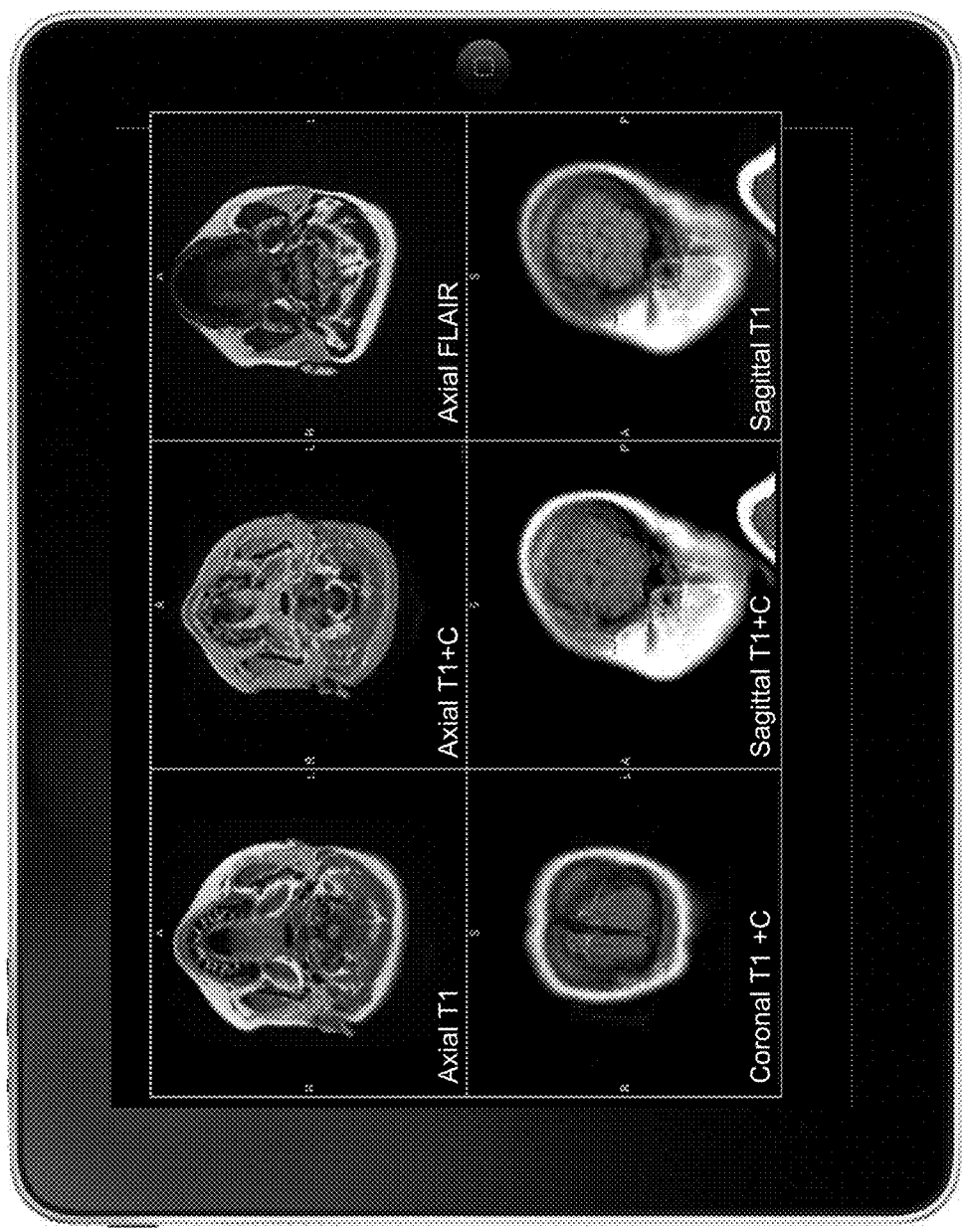
FIG. 15 illustrates a tablet device displaying the first six image series of the exam discussed with reference to FIG. 14.

FIG. 14 illustrates an arrangement of various image series, wherein six of the image series may be displayed on a display device (or multiple display devices) concurrently. In particular, view 1401 of FIG. 14 illustrates image series that are similar to those displayed in view 1320 of FIG. 13. However, as is illustrated in FIG. 14, the number of series exceeds the number of image frames displayed on the display device leaving four image series not displayed. FIG. 15 illustrates a tablet device displaying the first six image series of the exam.

In the example show in FIG. 14, a contrast enhanced brain MRI was performed with a clinical history of "Possible Brain Metastases." Selection 1401 indicates a portion of the series that are capable of being displayed currently on the display device, e.g., the example display device can display six series concurrently. In this embodiment, the image series are ordered by importance, arranged from top to bottom followed by left to right. In this example the order of series importance is Axial T1, Coronal T1+C, Axial T1+C, Sagittal T1+C, Axial FLAIR, Sagittal T1, Axial T2, Axial Diffusion, etc.

Selection 1410, displayed with a dashed line, outlines the first six series that might be first displayed automatically on the display device illustrated in FIG. 15, as shown. By interacting with the computing device, for example by using a left finger swipe on the touchscreen of a device, as illustrated in view 1030 of FIG. 10, the series displayed on the device could be changed. For example, a left swipe might display the series selection 1420, bringing in the next two series, in order of importance. Left and right swipes could conceptually move box 1420 left or right, displaying series of greater and lesser importance.

The systems and methods described herein may increase the accuracy of readers by presenting first the series that are most likely to be important in various clinical situations, directing the reader's attention to those series. In another embodiment, the series are arranged according to a series view order rather than (or in addition to) series importance. Other Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an Information Display Computing Device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of ordering a plurality of image series of a medical exam, the method comprising:
   determining, by one or more hardware computer processors executing computer-executable instructions stored on one or more non-transitory computer-readable storage mediums, a clinical indication associated with a medical exam, the medical exam including a set of three-dimensional (3D) imaging data;
   accessing, by the one or more hardware computer processors, interaction data including, for one or more previous medical exams associated with the clinical indication, indications of frequencies of images of respective series types of the previous medical exams being marked as important by a user designated as an expert with respect to medical exams associated with the clinical indication, wherein each respective series type indicates at least one of an imaging orientation, imaging modality, or an imaging plane;
   determining, based on the interaction data and by the one or more hardware computing processors, a first series type of the respective series types having a highest frequency of images previously marked as important;
   determining, based on the interaction data and by the one or more hardware computing processors, a second series type of the respective series types having a second highest frequency of images previously marked as important;
   determining, based on the interaction data and by the one or more hardware computing processors, a custom ordering of the respective series types, wherein the first series type is ordered first in the custom ordering, and wherein the second series type is ordered second in the custom ordering;
   reconstructing the set of 3D imaging data to generate, based on the custom ordering and by the one or more hardware computing processors, a plurality of image series each comprising a respective set of two-dimensional (2D) images, wherein:
      a first set of 2D images is reconstructed first from the set of 3D imaging data to generate a first image series of the first series type is reconstructed first, a second set of 2D images is reconstructed second from the set of 3D imaging data to generate a second image series of the second series type is reconstructed second, and the first set of 2D images is reconstructed before the second set of 2D images at least based on the first series type being ordered before the second series type in the custom ordering; and transmitting an indication of the custom ordering to a remote computing device to cause the remote computing device to display the plurality of image series in an order indicated in the custom ordering, wherein the indication causes 2D images of the first image series to be displayed before 2D images of the second image series.

2. The method of claim 1 further comprising processing, with computer aided diagnostics and by the one or more hardware computer processors, the plurality of image series in the order indicated in the custom ordering.

3. The method of claim 1, wherein an image marked as important is indicated by at least one of:
the image being added to a montage;
the image being marked as a key image;
the image being selected for display in a particular order with respect to other images;
a measurement being performed on the image; or
the image being selected for inclusion in a report.

4. The method of claim 1, wherein the interaction data further includes interaction data of a group of users, wherein the interaction data of the group of users indicates, for at least one of the one or more previous medical exams associated with the determined clinical indication, indications of frequencies of images of each respective series type of the previous medical exam being marked as important by users of the group of users.

5. The method of claim 4, wherein the custom ordering is determined based on the user interaction data of the group of users, wherein the method further comprises:
displaying, to a particular user of the group of users and on an electronic display, the plurality of image series in the order indicated by the custom ordering.

6. The method of claim 1, further comprising:
visually distinguishing particular ones of the plurality of image series based on the prioritization of the plurality of image series.

7. The method of claim 1, further comprising:
transmitting the indication of the custom ordering to the remote computing device to cause the remote computing device to preload the plurality of image series in the order indicated in the custom ordering, wherein the indication causes the first set of 2D images to be preloaded before the second set of 2D images.

8. A method comprising:
determining, by one or more processors executing computer-executable instructions, a clinical indication of a medical exam, the medical exam including a set of three-dimensional imaging data;
identifying, by the one or more processors, interaction data associated with the determined clinical indication, the interaction data indicating, for one or more previous medical exams associated with the determined clinical indication, indications of frequencies of images of respective series types of the previous medical exam being marked as important by one or more experts, wherein the one or more experts are experts with respect to medical exams associated with the determined clinical indication, wherein each respective series type indicates at least one of an imaging orientation, imaging modality, or an imaging plane;

determining, based on the identified interaction data, a prioritization of the respective series types, wherein, in the prioritization, a first series type comes before a second series type, wherein images of the first series type of the previous medical exams are marked as important more frequently than images of the second series type of the previous medical exams;

reconstructing, based on the prioritization and by the one or more hardware computing processors, a plurality of image series from the set of three-dimensional imaging data, the plurality of image series each comprising a respective set of two-dimensional images, wherein:

a first set of 2D images is reconstructed first from the set of 3D imaging data to generate a first image series of the first series type, a second set of 2D images is reconstructed second from the set of 3D imaging data to generate a second image series of the second series type, and the first set of 2D images is reconstructed before the second set of 2D images at least based on the first series type being ordered before the second series type in the prioritization; and transmitting an indication of the prioritization to a remote computing device to cause the remote computing device to display the plurality of image series in an order indicated by the prioritization, wherein the indication causes 2D images of the first image series to be displayed before 2D images of the second image series.

9. The method of claim 8, wherein the one or more experts comprise users associated with a same group, or users associated with a same specialty.

10. The method of claim 8, wherein an image marked as important comprises is indicated by at least one of:
the image being added to a montage,
the image being marked as a key image,
the image being selected for display in a particular order with respect to other images,
a measurement being performed on the image, or the image being selected for inclusion in a report.

11. The method of claim 10, wherein the interaction data comprises importance scores for respective image series associated with medical exams having the determined clinical indication.

12. The method of claim 11, wherein importance scores for respective image series are weighted based on a quantity of images of respective image series that are marked as important.

13. The method of claim 8, further comprising:
using the prioritization of the respective series types in order to perform at least one of:
processing image series of the medical exam with computer aided diagnostics;
highlighting image series of the medical exam; or
updating an imaging protocol.

14. The method of claim 13, wherein use of the prioritization is further determined based on user preferences, group preferences, site preferences, system preferences, and/or default software preferences.

15. The method of claim 8, wherein the plurality of image series are further displayed according to a hanging protocol preferred by a user.

16. The method of claim 8, wherein the plurality of image series are further displayed according to a hanging protocol preferred by a user, and wherein the method further comprises:
visually distinguishing particular ones of the plurality of image series based on the prioritization of the plurality of image series.

17. The method of claim 8, further comprising:
transmitting the indication of the prioritization to the remote computing device to cause the remote computing device to preload the plurality of image series in the order indicated by the prioritization, wherein the indication causes the first set of 2D images to be preloaded before the second set of 2D images.

18. A computing system comprising:
one or more hardware computer processors configured to execute software instructions in order to at least:
determine a clinical indication associated with a medical exam, the medical exam including a set of three-dimensional (3D) imaging data;
gather interaction data of a plurality of users with a plurality of previous medical exams, wherein:
each of the medical exams includes a plurality of image series each associated with a series type,
each series type indicates at least one of an imaging orientation, imaging modality, or an imaging plane,
each image series includes a plurality of images,
the interaction data indicates frequencies of images of each series type of the previous medical exams being marked as important by users, and
the users include experts as to reviewing the previous medical exams;
determine, based on interaction data indicating frequencies of images of each series type of the plurality of medical exams being marked as important, a prioritization of the plurality of image series types;
based on the prioritization, update an imaging protocol such that an image series type having a lowest priority is removed from the imaging protocol;
reconstruct the set of 3D imaging data to generate, based on the imaging protocol, a group of image series each comprising a respective set of two-dimensional (2D) images, wherein:
a first set of 2D images is reconstructed first from the set of 3D imaging data to generate a first image series of the first series type,
a second set of 2D images is reconstructed second from the set of 3D imaging data to generate a second image series of the second series type,
the first set of 2D images is reconstructed before the second set of 2D images at least based on the first series type being ordered before the second series type in the prioritization, and
the group of image series does not include an image series with the image series type having the lowest priority; and
transmit an indication of the prioritization to a remote computing device to cause the remote computing device to display the group of image series in an order indicated by the prioritization, wherein the indication causes 2D images of the first image series to be displayed before 2D images of the second image series.

19. The computer system of claim 18, wherein the one or more hardware computer processors are further configured to the execute software instructions in order to:
transmit the indication of the prioritization to the remote computing device to cause the remote computing device to preload the plurality of image series in the order indicated by the prioritization, wherein the indication causes the first set of 2D images to be preloaded before the second set of 2D images.

20. A non-transitory computer-readable storage medium storing software instructions that, in response to execution by a computer system having one or more hardware processors, configure the computer system to perform operations comprising:
determining a clinical indication of a medical exam, the medical exam including a set of three-dimensional (3D) imaging data;
identifying interaction data associated with the determined clinical indication, the interaction data indicating, for one or more previous medical exams associated with the determined clinical indication, indications of frequencies of images of respective series types of the previous medical exam being marked as important by one or more experts, wherein the one or more experts are experts with respect to medical exams associated with the determined clinical indication;
determining, based on the identified interaction data, a prioritization of the respective image types, wherein, in the prioritization, a first series type comes before a second series type, wherein images of the first series type of the previous medical exams are marked as important more frequently than images of the second series type of the previous medical exams;
reconstructing the set of 3D imaging data to generate, based on the prioritization and by the one or more hardware computing processors, a plurality of image series each comprising a respective set of two-dimensional (2D) images, wherein:
a first set of 2D images is reconstructed first from the set of 3D imaging data to generate a first image series of the first series type,
a second set of 2D images is reconstructed second from the set of 3D imaging data to generate a second image series of the second series type, and
the first set of 2D images is reconstructed before the second set of 2D images at least based on the first series type being ordered before the second series type in the prioritization; and
transmitting an indication of the prioritization to a remote computing device to cause the remote computing device to display the plurality of image series in an order indicated by the prioritization, wherein the indication causes 2D images of the first image series to be displayed before 2D images of the second image series.

21. The non-transitory computer-readable storage medium in claim 20, wherein the software instructions further configure the computer system to perform operations comprising:
transmitting the indication of the prioritization to the remote computing device to cause the remote computing device to preload the plurality of image series in the order indicated in the prioritization, wherein the indication causes the first set of 2D images to be preloaded before the second set of 2D images.

* * * * *